(12) United States Patent
Decker et al.

(10) Patent No.: US 9,192,505 B2
(45) Date of Patent: Nov. 24, 2015

(54) CUSTOM REDUCTION SPLINT FOR EDENTULOUS PATIENTS

(71) Applicants: Summer Joy Decker, Apollo Beach, FL (US); Jonathan Michael Ford, Apollo Beach, FL (US); Jessica Allen Ching, Tampa, FL (US)

(72) Inventors: Summer Joy Decker, Apollo Beach, FL (US); Jonathan Michael Ford, Apollo Beach, FL (US); Jessica Allen Ching, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/629,074

(22) Filed: Feb. 23, 2015

(65) Prior Publication Data

US 2015/0238345 A1    Aug. 27, 2015

Related U.S. Application Data

(60) Provisional application No. 61/943,636, filed on Feb. 24, 2014.

(51) Int. Cl.
| | |
|---|---|
| *G06K 9/00* | (2006.01) |
| *A61F 5/058* | (2006.01) |
| *A61B 6/14* | (2006.01) |
| *A61B 6/03* | (2006.01) |
| *A61B 5/055* | (2006.01) |
| *A61C 5/14* | (2006.01) |
| *A61M 1/00* | (2006.01) |
| *G06T 7/00* | (2006.01) |

(52) U.S. Cl.
CPC ............. *A61F 5/05891* (2013.01); *A61B 5/055* (2013.01); *A61B 6/032* (2013.01); *A61B 6/037* (2013.01); *A61B 6/14* (2013.01); *A61C 5/14* (2013.01); *A61M 1/0023* (2013.01); *G06T 7/00* (2013.01); *A61M 2207/10* (2013.01); *G06T 2207/30036* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 6,086,365 A | 7/2000 | Fields | |
| 6,227,861 B1 | 5/2001 | Cartledge et al. | |
| 6,671,539 B2 | 12/2003 | Gateno et al. | |
| 7,874,836 B2 * | 1/2011 | McSurdy, Jr. | 433/6 |
| 8,246,663 B2 | 8/2012 | Lovald et al. | |

(Continued)

OTHER PUBLICATIONS

Metzger et al., Manufacturing splints for orthognathic surgery using a three-dimensional printer. Oral Surgery, Oral Medicine, Oral Pathology, Oral Radiology, and Endodontology. Feb. 2008. vol. 105: e1-e7.

(Continued)

*Primary Examiner* — Vu Le
*Assistant Examiner* — Samah Beg
(74) *Attorney, Agent, or Firm* — Nilay J. Choksi; Smith & Hopen, P.A.

(57) ABSTRACT

A custom oral splint that is operatively secured to the maxilla and mandible of a subject/patient to assist in reduction and provide maintenance of reduction of maxillary and mandibular fractures in the edentulous or partially edentulous subject/patient. In this difficult patient population, there are very limited options for maxillomandibular fixation, and none provide stable reduction of fractures. The novel device minimizes operative time and equipment, as well as offers the ability to transition the patient from rigid fixation to elastics postoperatively. The novel device is custom-designed for each patient's degree of bone atrophy, ensuring a high quality, and effective product.

20 Claims, 49 Drawing Sheets
(43 of 49 Drawing Sheet(s) Filed in Color)

(56) References Cited

U.S. PATENT DOCUMENTS

| | | |
|---|---|---|
| 8,282,635 B1 | 10/2012 | Amato |
| 8,562,346 B2 * | 10/2013 | Collins et al. ............... 433/173 |
| 2003/0065259 A1 * | 4/2003 | Gateno et al. ............... 600/425 |
| 2007/0056467 A1 * | 3/2007 | Panzera ........................ 106/35 |
| 2007/0074729 A1 | 4/2007 | Magnin |
| 2007/0190481 A1 * | 8/2007 | Schmitt ......................... 433/68 |
| 2007/0190492 A1 * | 8/2007 | Schmitt ........................ 433/213 |
| 2008/0056439 A1 * | 3/2008 | Thompson et al. ............ 378/15 |
| 2009/0248184 A1 * | 10/2009 | Steingart et al. .............. 700/98 |
| 2011/0166572 A1 | 7/2011 | Ihde |
| 2012/0028221 A1 * | 2/2012 | Williams ...................... 433/215 |
| 2012/0179281 A1 * | 7/2012 | Steingart et al. .............. 700/97 |
| 2012/0214121 A1 | 8/2012 | Greenberg |
| 2013/0310963 A1 | 11/2013 | Davison |
| 2014/0370465 A1 * | 12/2014 | Lucas ........................... 433/214 |
| 2015/0083140 A1 | 3/2015 | Youngman et al. |
| 2015/0132716 A1 * | 5/2015 | Kusch et al. .................. 433/140 |

OTHER PUBLICATIONS

Kocabay et al., The conservative treatment of pediatric mandibular fracture with prefabricated surgical splint: a case report. Dental Traumatology. Aug. 2007. vol. 23: 247-250.

International Search Report and Written Opinion for PCT/US2012/017126 (filing date: Feb. 23, 2015) with a mailing date of Jun. 12, 2015; Applicant: University of South Florida.

* cited by examiner

CUSTOM REDUCTION SPLINT FOR EDENTULOUS PATIENTS

CROSS-REFERENCE TO RELATED APPLICATIONS

This nonprovisional application is a continuation of and claims priority to U.S. Provisional Application No. 61/943,636, entitled "Custom Reduction Splint for Edentulous and Partially Edentulous Patients", filed Feb. 24, 2014 by the same inventors, the entirety of which is incorporated herein by reference.

BACKGROUND OF THE INVENTION

1. Field of the Invention

This invention relates, generally, to oral splints. More specifically, it relates to the reduction and maintenance of reduction in mandible and/or maxilla fractures of edentulous or partially edentulous patients.

2. Brief Description of the Prior Art

Oral splints are commonly known in the art, including those utilized for fixation of the jaw during recovery from mandibular or maxillary fractures. For example, U.S. Pat. No. 6,227,861 to Cartledge et al. discusses a pre-formed mandible splint and a method of aligning and stabilizing a fractured mandible with such a splint. The splint approximates the curvature of the lower teeth or gingiva of the lower jaw. The splint is U-shaped, follows the human dentition, and has rows of holes or slots along its outer and inner perimeter. The splint is placed on the teeth and wired through the holes or slots to the mandible to align the mandible. Fractures are then to be screwed into place according to the curvature of the splint. Cartledge attempts to improve upon the art by eliminating the need of wiring the patient's jaw shut. However, the splint of Cartledge is pre-formed and is intended to uniformly fit the population, and thus is not contoured to each patient's anatomy, but rather provides a singular, uniform flat surface in contact with variable anatomy. As the splint is in a fixed, straight plane, the patient's teeth may not all be at the same height in order to make adequate contact with the splint. Inconsistent dental height between adjacent teeth is common, especially in partially edentulous patients. Partially edentulous patients often have gaps between teeth from missing teeth. Any areas of missing teeth can lead to lengthening of the opposing tooth, as it does not have proper occlusal contact. For example, if a mandibular lateral incisor is absent, the opposing maxillary dentition will lack normal occlusal contact, which can result in lengthening of the opposing maxillary tooth. This further adds to any height discrepancies between teeth and leads to areas of non-contact between the tooth and splint, ultimately causing fracture malreduction. As such, Cartledge fails to provide either equally distributed contact or stability of fracture reduction. Further, the splint of Cartledge does not address the occlusion of the patient. If the splint rests in contact with dentition, it interferes with proper occlusion, which is the primary objective in fracture reduction. If the splint rests in contact with the gingiva directly, as in the case of an edentulous patient, then the proper distance is not maintained for the patient to wear their denture appliance postoperatively. Also, the Cartledge device is designed only for tooth-bearing regions of the mandible, including fractures of the symphysis, parasymphysis, and body. The device does not assist in reduction of mandible fractures of the angle, ramus, condyle or coronoid.

Additionally, U.S. Pat. No. 6,671,539 to Gateno et al. describes a method of forming a surgical splint to receive a patient's dentition and align the upper jaw and the lower jaw during surgery. The method disclosed includes generating a computed tomography (CT) computer model of bone structure, generating a digital dental computer model of the patient's dentition, and combining the CT computer model and the digital dental computer model to form a composite computer model. The upper jaw and lower jaw are repositioned to form a "planned position" computer model. Thereafter, a computer model of the surgical splint is formed to direct fabrication of the splint. However, this methodology is quite complex and involves multiple steps, including separate dental trays, dental modeling, and merging of the facial bone CT with dental CT data. This can become very time-consuming and inefficient in the fabrication of the splint. This device also does not address fracture reduction but rather is for craniofacial and maxillofacial deformities requiring osteotomies, which is not used for fracture reduction. The device also does not address postoperative maintenance of the surgical splint. The device does not appear to be designed to remain in place postoperatively, but rather serves only as an intraoperative device.

U.S. Pat. No. 6,086,365 to Fields discusses fracture reduction and maxillary fixation by using a dental splint that is cemented directly to the patient's teeth to immobilize the patient's jaw during and following oral surgery. The splint includes an arch band having a back side that receives the bonding cement and a facial side from which multiple ligature studs project for engaging ligature wires. The arch band further includes flow passages that permit bonding cement deposited on the back side to flow onto the facial side as the arch band is pressed against the patient's teeth. However, this device is not personalized for individual patient and also requires bonding to the patients teeth. As it requires bonding to teeth, the device cannot be used in edentulous patients. Furthermore, the postoperative stability of the device is limited by the relative strength of the bonding agent used.

U.S. Patent Application Publication No. 2007/0074729 to Magnin describes a mandibular advancement splint used to treat snoring and sleep apnea. The splint is formed of two thermoformable trays designed to envelop the upper and lower arch. In order to adapt to individual variations in teeth, the splint includes an articulated frame having rigid and flexible elements, immersed in the thermoformable flexible material or molded around it. However, as indicated, the device is incapable of assisting with fracture reduction and is constructed of a thermoformable tray. This device is also only used while sleeping.

Metzger et al. (Marc Christian Metzger. Bettina Hohlweg-Majert, Uli Schwarz, Matthias Teschner, Beat Hammer, Rainer Schmelzeisen, Manufacturing splints for orthognathic surgery using a three-dimensional printer, Oral Surgery, Oral Medicine, Oral Pathology, Oral Radiology, and Endodontology, Volume 105, Issue 2, February 2008, Pages e1-e7, ISSN 1079-2104) discusses the use of various tomographic techniques to produce a virtual rendering of a patient's jaw in order to produce splints for orthognathic surgery using a 3D printer. Data is acquired from the patient with orthognathic deformation via CT scan or cone beam computed tomography (CBCT) scan. The jaws are virtually repositioned and encoded, followed by printing of the splint. However, this device fabrication requires a separate dental scan or scanning of plaster dental models, the information of which is then incorporated into a facial bones CT scan. The device also addresses orthognathic surgical procedures, rather than reduction of maxillary or mandibular fractures and is incapable of performing as such. Further, the device utilizes intraoperative splints, but does not comment on the ability of the splint to remain postoperatively. The device can only be used in patients with dentition and thus cannot be applied to partially or completely edentulous patients.

Kocabay et al. (Ceyda Kocabay, Mustafa Sancar Ataç, Burak Öner, Nadir Güngör, The conservative treatment of pediatric mandibular fracture with prefabricated surgical splint: a case report, Dental Traumatology Volume 23, Issue 4, pages 247-250, August 2007) discusses the use of a preformed surgical splint for mandibular fracture fixation. This publication discusses the development of a custom, preformed splint for mandibular fracture fixation though the use of pressure molds. The device utilizes plaster dental modeling for formation of the acrylic splint, which can hinder the availability of the splint for operative use. The device further requires dentition to maintain fracture stability, and thus does not have application to partially or completely edentulous patients.

In the case described by Kocabay et al., the fracture was a midline symphyseal mandible fracture. In this type of fracture, the rotational forces are minimal. In all other types of mandibular fractures, the rotational forces acting to disrupt fracture alignment are much greater. As the device is depicted, it is unlikely the acrylic splint alone could maintain fracture reduction with these strong, additional rotation forces characteristic of mandibular fractures. The device is illustrated in a pediatric fracture, which is likely a greenstick fracture, as the authors acknowledge. This means that the periosteum overlying the fractured bone remains intact on at least one side. With intact periosteum from a greenstick fracture, reduction of the fracture becomes significantly easier than when the entire periosteum is disrupted and the fracture segments are freely mobile. In the adult patient, greenstick fractures are not seen, but rather, the entire periosteum is disrupted. Thus, in an adult fracture, it is doubtful that the acrylic splint would reduce the fracture and maintain postoperative alignment.

Generally, in difficult patient populations, such as those with edentulism or partial edentulism, there are very limited options for maxillomandibular fixation, and none provide stable reduction of fractures, including the foregoing devices and methodologies discussed. What is currently practiced in the art for an edentulous and partially edentulous patient with dentures, is that the patient's jaw is imaged upon removal of the dentures to ensure that the dentures are not blocking any visible fractures or other dentition. In many cases, the dentures are worn down and thus are not positioned where the patient's jaws should be aligned. As a result, the patient's jaw may have collapsed to an extent. To maintain the jaw in place then, the dentures are drilled or screwed into place since there is no other manner of estimating the spacing between the maxilla and mandible. This destroys the dentures for any future use and forces the patient to purchase a new set of expensive dentures.

Accordingly, what is needed is an improved reduction splint, and method of fabrication thereof, for edentulous and partially edentulous subjects or patients. However, in view of the art considered as a whole at the time the present invention was made, it was not obvious to those of ordinary skill in the field of this invention how the shortcomings of the prior art could be overcome.

All referenced publications are incorporated herein by reference in their entireties. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a patient-specific oral splint for edentulous patients is now met by a new, useful, and nonobvious invention.

In an embodiment, the current invention is a method of fabricating an oral splint for reduction of an oral fracture in an edentulous or partially edentulous subject or patient (herein "subject"). A jaw of the subject is scanned or imaged, and the results are imported into a software program/application that segments the maxilla and mandible of the jaw. In the software program, the fracture in the jaw is realigned into a normal or unfractured position. The upper palate of the jaw is outlined, as is the lower palate of the jaw. The distances between the outlines is interpolated, and that distance is indicated as the initial splint configuration. At this point, the bone and dentition of the maxilla and mandible can be removed from the image of the jaw, and the initial splint configuration can be split into a maxillary splint and a mandibular splint, thus forming a virtual image of the resulting oral splint.

Upon importing the imaging results into the software program, the maxilla and mandible may be tessellated into a three-dimensional model.

The initial splint configuration may be expanded outwardly so that the mandible and maxilla of the subject can fit snugly or be contained therewithin.

An evacuation aperture may be formed in an anterior portion of the initial splint configuration, such that an upper portion of the evacuation aperture is disposed in the anterior portion of the maxillary splint and a lower portion of the evacuation aperture is disposed in the anterior portion of the mandibular splint.

The step of splitting the initial splint configuration into the maxillary and mandibular splints can be performed by positioning an anterior-posterior plane within a midsection of the initial splint configuration. The position of the plane in a cranial-caudal direction is based on the presence or absence of teeth within the jaw of the subject. In this case, the maxillary and mandibular splints can be split along this plane.

An extrusion can be disposed on a superior surface of the mandibular splint or on an inferior surface of the maxillary splint. A channel would then be disposed on the splint that did not receive the extrusion. The extrusion and channel would correspond positionally and dimensionally, so that a tongue and groove fitting is formed between the maxillary and mandibular splints. In a further embodiment, both the extrusion and channel are U-shaped along a jawline of the subject.

A plurality of wire apertures may be formed in the maxillary and mandibular splints to accommodate wiring to secure the maxillary and mandibular splints to the maxilla and mandible, respectively.

Projections may be disposed on the left and right sides of the maxillary splint, and projections may be disposed on the left and right sides of the mandibular splint. The projections on the maxillary splint may be aligned with the projections on the mandibular splint to facilitate wiring.

The step of fabricating the oral splint based on the virtual image of the oral splint may be performed by transmitting the virtual image to a three-dimensional printer for printing the oral splint.

An upper edge and/or lower edge of the initial splint configuration may be trimmed or filed down to better fit the jaw and soft tissue of the subject or patient (i.e., correcting for gum line, etc.)

If the subject or patient is edentulous or partially edentulous, which may cause over rotation of the mandible when approximating the anterior edges of the maxilla and mandible, a spacer may be positioned on the mandible and/or maxilla (wherever dentition is absent) in order to provide proper spacing between the subject or patient's mandible and maxilla.

In a separate embodiment, the current invention is a surgical technique for reduction of an oral fracture in an edentulous or partially edentulous subject. The mandible and maxilla of the subject is scanned or imaged, and the results are imported into a software program/application that segments the maxilla and mandible of the jaw. In the software program, the fracture or fractures in the jaw (made up of the mandible and/or maxilla) are realigned into a normal or unfractured position. The upper palate of the jaw is outlined, as is the lower palate of the jaw. The distances between the outlines is interpolated, and that distance is indicated as the initial splint configuration. At this point, the bone and dentition of the maxilla and mandible can be removed from the image of the jaw, and the initial splint configuration can be split into a maxillary splint and a mandibular splint, thus forming a virtual image of the resulting oral splint. Once the physical splint has been fabricated, the maxillary splint is positioned and secured on the maxilla of the subject with the maxilla and its fractures in a reduced position. Similarly, the mandibular splint is positioned and secured on the mandible of the subject with the mandible and its fractures in a reduced position.

Upon importing the imaging results into the software program, the maxilla and mandible may be tessellated into a three-dimensional model.

The initial splint configuration may be expanded outwardly so that the mandible and maxilla of the subject can fit snugly or be contained therewithin.

An evacuation aperture may be formed in an anterior portion of the initial splint configuration, such that an upper portion of the evacuation aperture is disposed in the anterior portion of the maxillary splint and a lower portion of the evacuation aperture is disposed in the anterior portion of the mandibular splint.

The step of splitting the initial splint configuration into the maxillary and mandibular splints can be performed by positioning an anterior-posterior plane within a midsection of the initial splint configuration. The position of the plane in a cranial-caudal direction is based on the presence or absence of teeth within the jaw of the subject. In this case, the maxillary and mandibular splints can be split along this plane.

An extrusion can be disposed on a superior surface of the mandibular splint or on an inferior surface of the maxillary splint. A channel would then be disposed on the splint that did not receive the extrusion. The extrusion and channel would correspond positionally and dimensionally, so that a tongue and groove fitting is formed between the maxillary and mandibular splints. In a further embodiment, both the extrusion and channel are U-shaped along a jawline of the subject.

A plurality of wire apertures may be formed in the maxillary and mandibular splints to accommodate wiring to secure the maxillary and mandibular splints to the maxilla and mandible, respectively.

The step of fabricating the oral splint based on the virtual image of the oral splint may be performed by transmitting the virtual image to a three-dimensional printer for printing the oral splint.

Projections may be disposed on the left and right sides of the maxillary splint, and projections may be disposed on the left and right sides of the mandibular splint. The projections on the maxillary splint may align with the projections on the mandibular splint to facilitate wiring, if desired. In a further embodiment, the maxillary and mandibular splints can be secured to each other via intersplint wires wrapped around the corresponding projections on the maxillary and mandibular splints.

The step of securing the maxillary splint onto the maxilla of the subject may be performed by pyriform drop wire and/or transpalatal-pyriform wire. The step of securing the mandibular splint onto the mandible of the subject may be performed by circummandibular wires via use of an awl or similar method.

An upper edge and/or lower edge of the initial splint configuration may be trimmed to better fit the jaw of the subject or patient (i.e., correcting for gum line, etc.)

If the subject or patient is edentulous or partially edentulous, which may cause over rotation of the mandible when approximating the anterior edges of the maxilla and mandible, a spacer may be positioned on the mandible and/or maxilla (wherever dentition is absent) in order to provide proper spacing between the subject or patient's maxilla and mandible.

In a separate embodiment, the current invention is a method of fabricating an oral splint and/or surgical technique for reduction of one or multiple fractures of the maxilla and/or mandible in an edentulous or partially edentulous subject or patient, using any one or more (or even all) of the foregoing limitations. Optionally, the outlining of the upper and lower palates, and interpolation thereof, prior to forming the initial splint configuration can be performed as follows. The upper palate of the jaw is outlined. The maxilla and mandible are also individually outlined. The distance between the three outlines (upper palate, maxilla, and mandible) is then interpolated and indicated to form the initial splint configuration.

It is an object of an embodiment of the current invention to provide both equally distributed contact between the maxilla and mandible and also provide stability of fracture reduction.

It is an object of an embodiment of the current invention to maintain proper distance between the mandible and maxilla, individualized for each patient, to ensure that when the fracture heals, the patient may resume wearing any previous dental appliance (e.g., dentures) without modification. This includes avoiding use of existing dental appliance for fracture stabilization, as this frequently leads to damaging of the device.

It is an object of an embodiment of the current invention to reduce fractures of the entire maxilla and mandible, including the condyle, as the current device is customized to the patient's anatomy and accounts for the relationship of the mandible to the maxilla.

It is an object of an embodiment of the current invention to fabricate an oral splint by performing one facial bone CT scan, digitally reducing the fractures, and printing the custom splint. Furthermore, the device may include predrilled holes, brackets (or projections), and space for suction in the splint itself.

It is an object of an embodiment of the current invention to provide a device designed with consideration of fracture reduction and patient safety, along with preservation postoperatively to assist in maintenance of fracture alignment.

It is an object of an embodiment of the current invention to utilize a facial bones CT scan and 3D printing, thus significantly expediting the availability of the splint for operative use.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIGS. 2B(a), 2B(b), and 2B(c) show the multi-step process for point registration.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the current invention is a methodology and/or device for a custom oral splint that is operatively secured to the maxilla and mandible to assist in fracture reduction. The methodology/device further provide maintenance of reduction of maxillary and mandibular fractures in the edentulous or partially edentulous patient. The methodology/device minimizes operative time and equipment in the operating room since pre-drilled positions and projections are placed in the splint beforehand, rather than having to perform this during operation. The device/methodology also offers the ability to transition the patient from rigid fixation to elastics postoperatively. The device can be custom-designed for each patient's degree of bone atrophy, ensuring a high quality and effective product.

Modeling and Printing

Figure 1A:
FIG. 1A is an axial CT image of a jaw fracture.
Figure 1B:
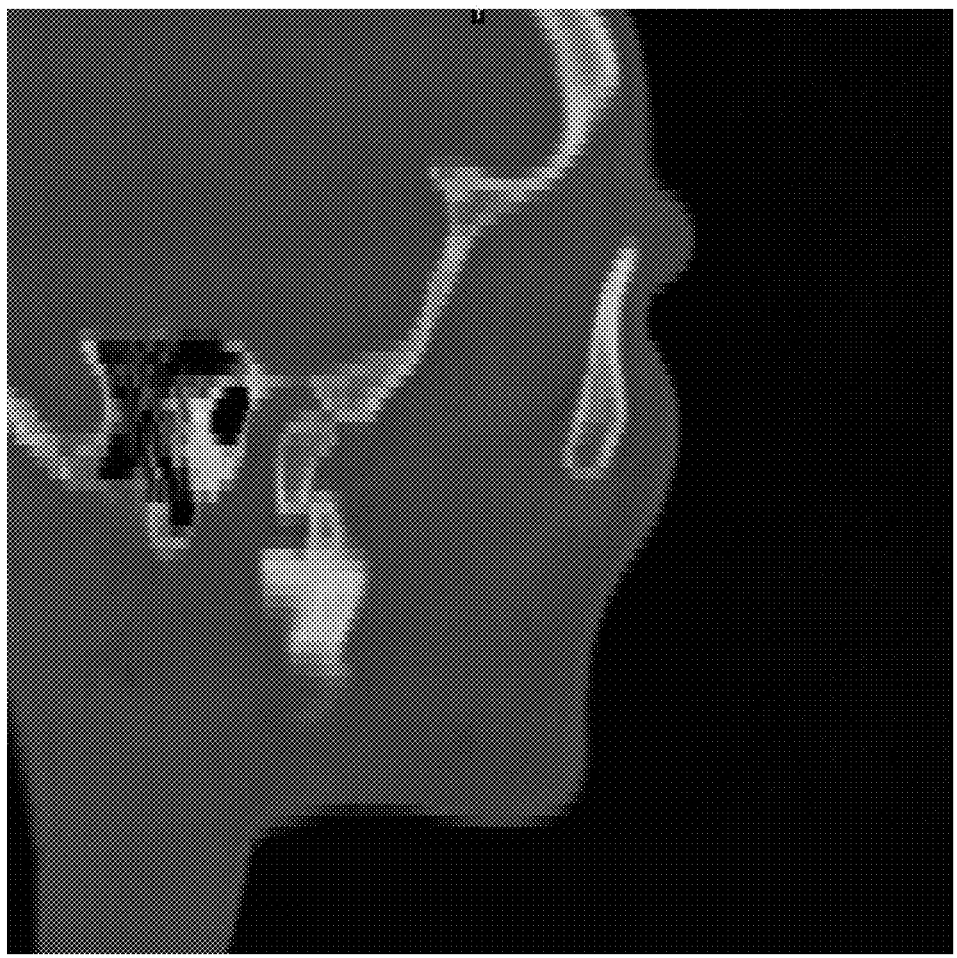
FIG. 1B is a sagittal CT image of the jaw fracture of FIG. 1A.
Figure 1C:
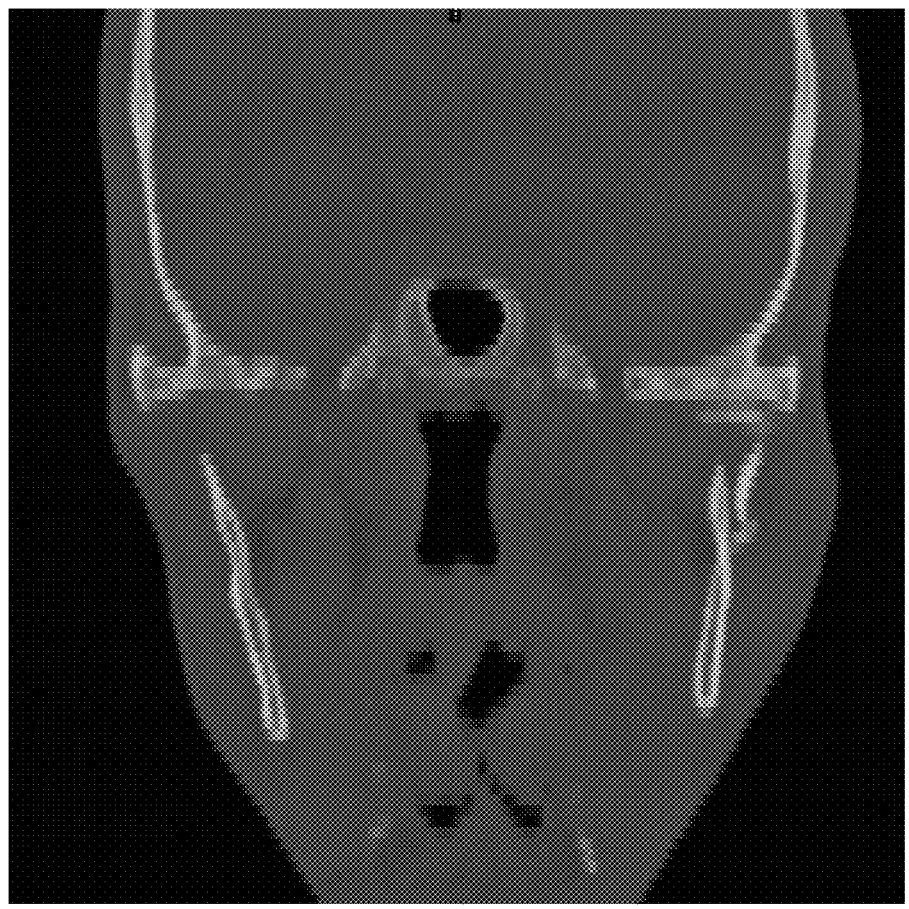
FIG. 1C is a coronal CT image of the jaw fracture of FIG. 1A.

The procedure begins with the patient's jaw being imaged, as can be seen in FIGS. 1A-1C. Any known imaging modality is contemplated herein. Examples include, but are not limited to, computed tomography (CT), positron emission tomography (PET), magnetic resonance imaging (MRI), x-ray, etc. In a particular embodiment, a CT scan can be used to image the patient's jaw. The CT scan or other imaging results are imported into any suitable medical image processing software package, for example MIMICS by MATERIALISE.

Figure 2A:
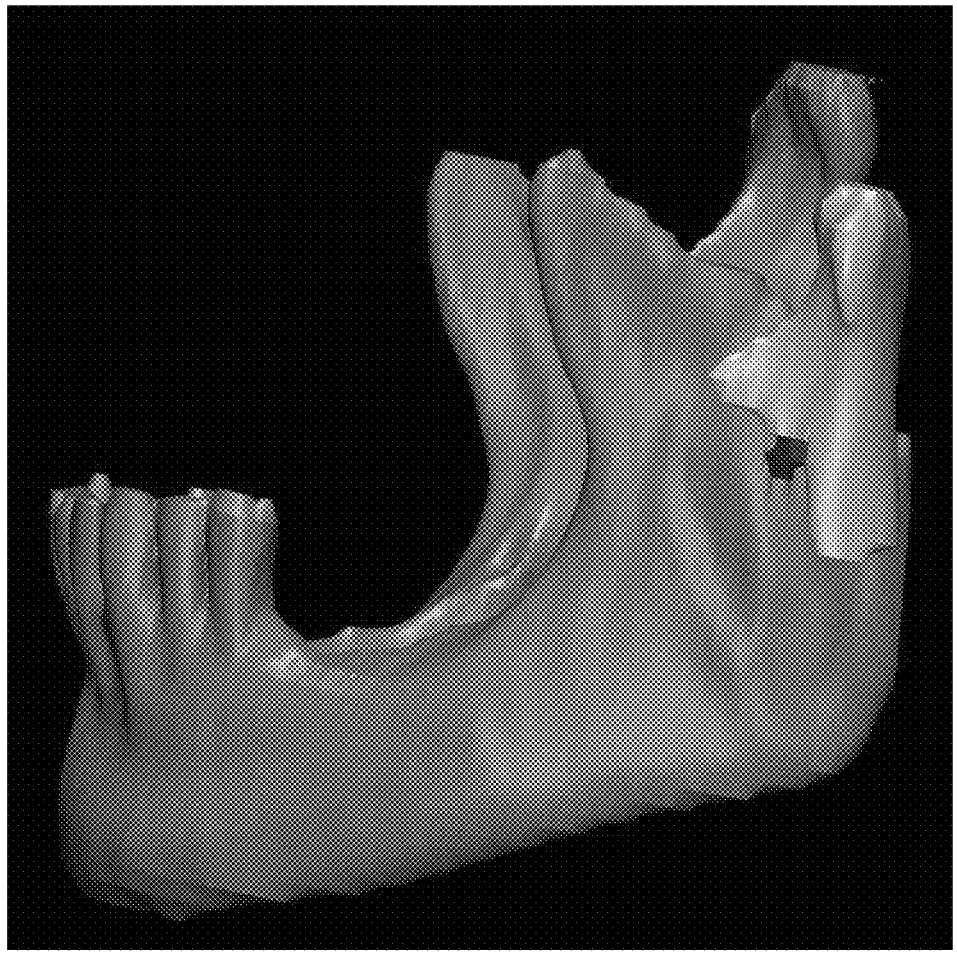
FIG. 2A is a 3D model/image/representation of a fractured jaw as seen in an image processing software program upon importation of the medical image into the software program.

Within the image on the image processing software program, the bone structures of the maxilla and mandible are segmented on the CT scan and then tessellated into three-dimensional models, as can be seen in FIG. 2A showing a jaw fracture. The broken or fractured bones are realigned virtually with the jaw as a whole, in particular the mandible, realigned, and placed into a "normal", healthy or unfractured position.

Figure 2B:
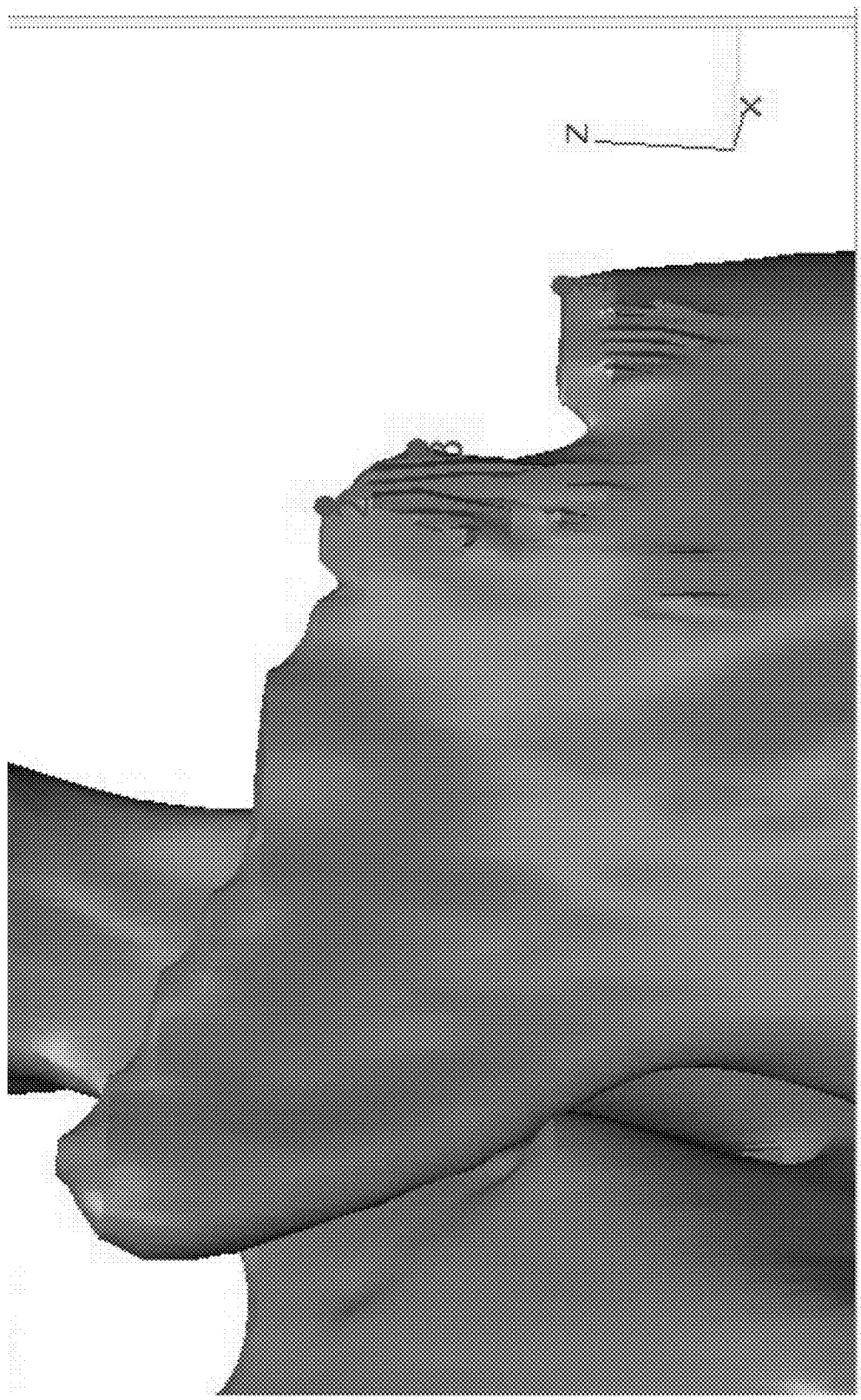
FIG. 2B depicts point registration in order to realign or reassemble the jaw of FIG. 2A and the fractured shards thereof.
Figure 2B:
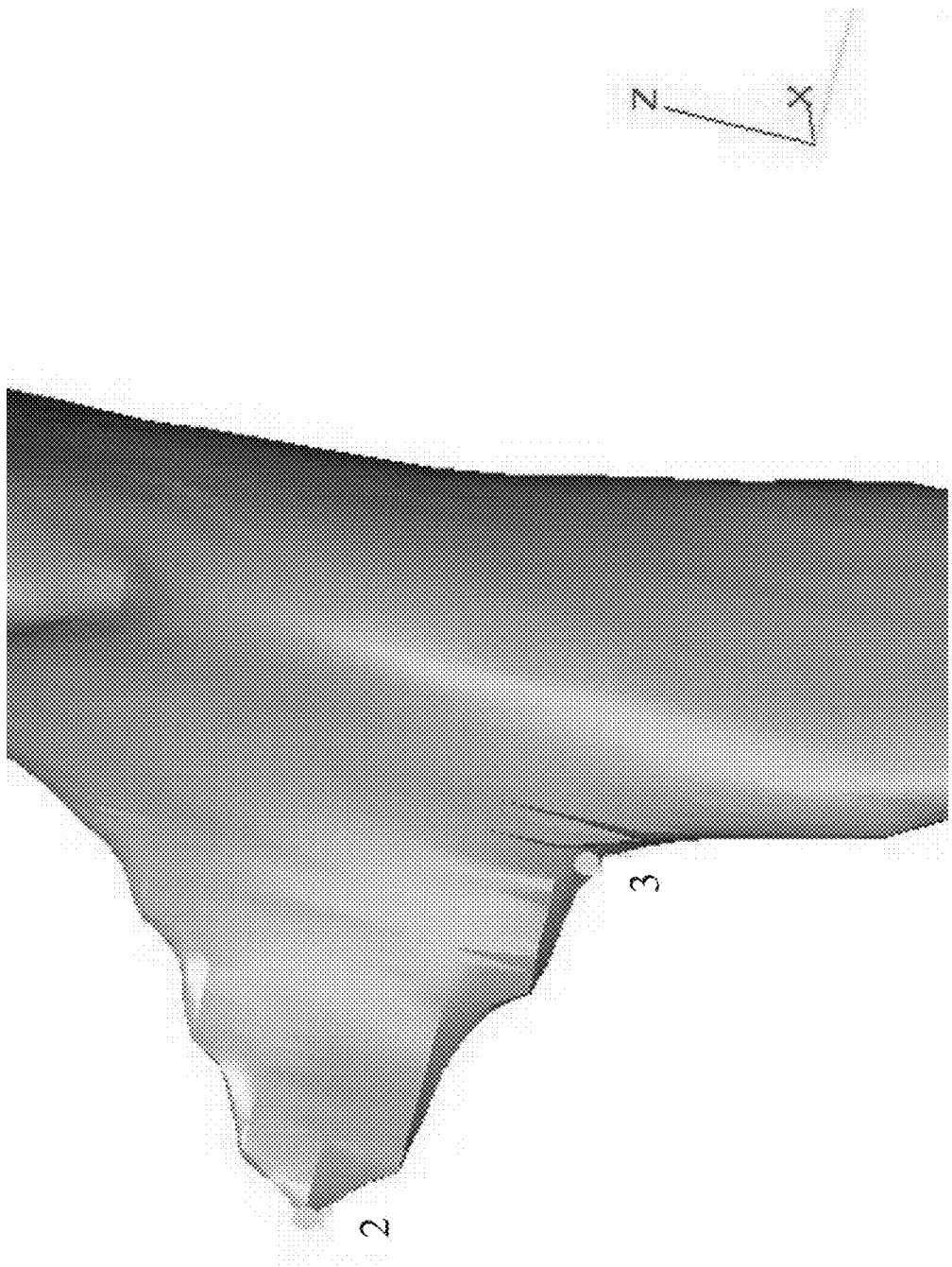
Figure 2B:
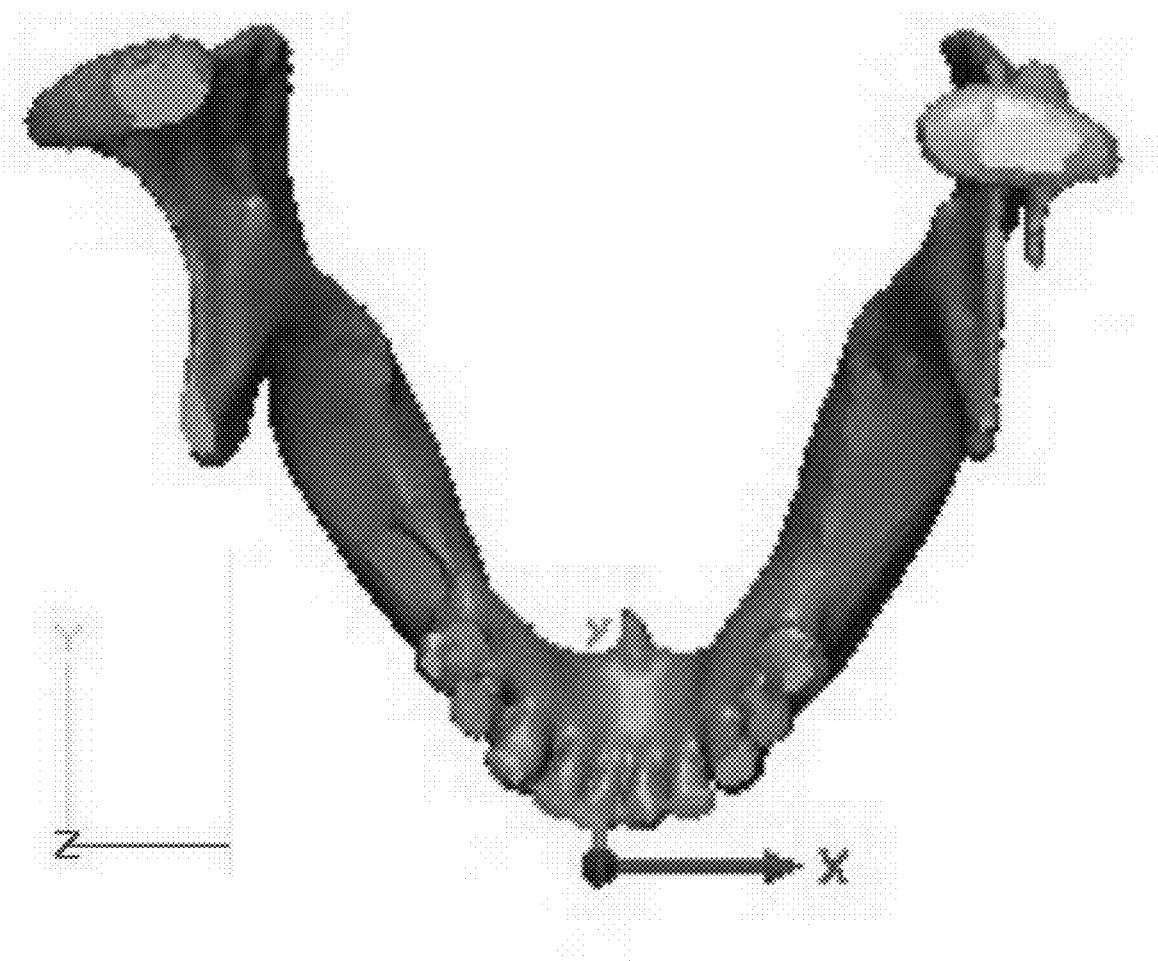

The fractured shards of the jaw can be realigned, for example, using point realignment or registration, which is shown in FIG. 2B, though any suitable methodology is contemplated herein. Point registration allows the fractured shards to be reassembled by placing a certain number of points on an initial surface (e.g., the jaw) (FIG. 2B(a)) and then placing corresponding points on the other surface (e.g., the jaw fragment) (FIG. 2B(b)) to which the initial surface is to be matched. A "best fit" can then be computed using those points to assemble the parts and thus realign the fractured shards in a normal or healthy position (FIG. 2B(c)).

Figure 2C:
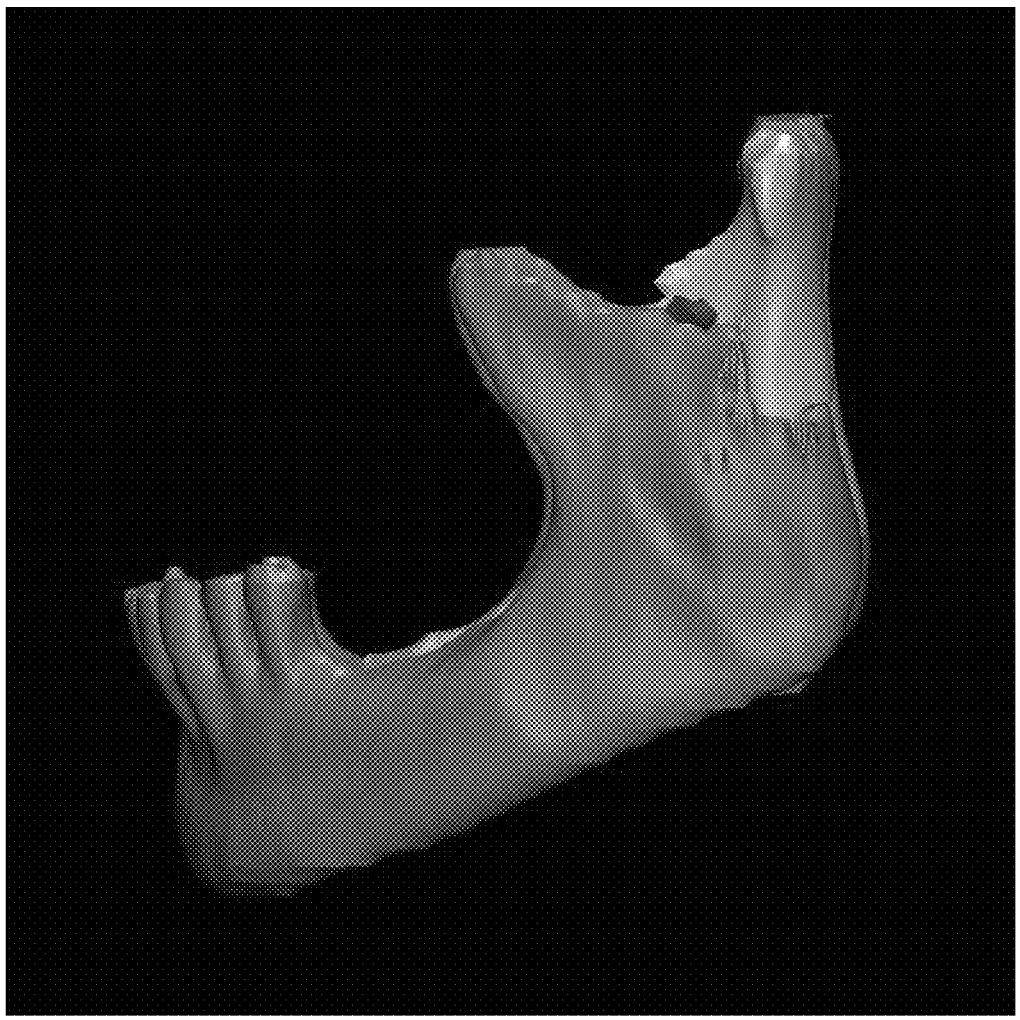
FIG. 2C is a 3D model/image/representation of a realigned jaw, corrected from the fractured jaw of FIG. 2A and resulting from the point realignment of FIG. 2B.
Figure 2D:
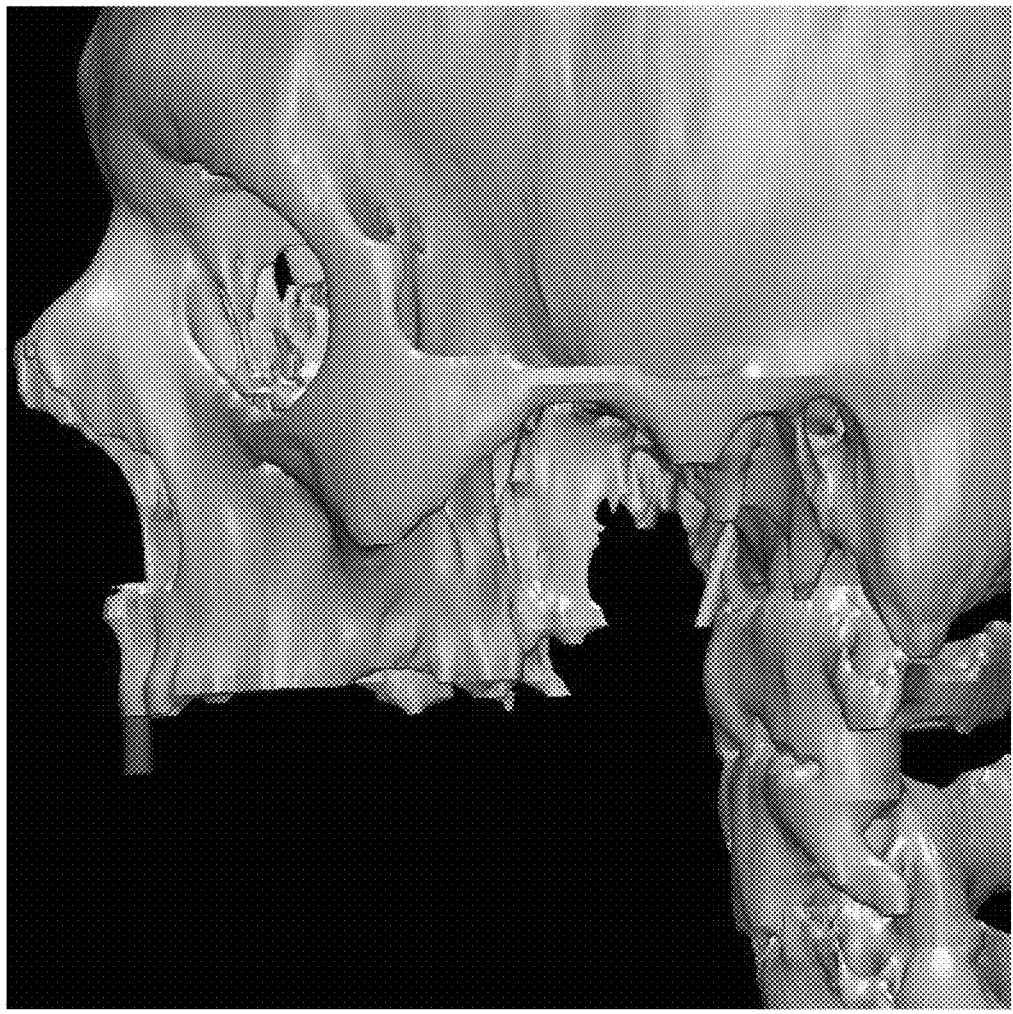
FIG. 2D depicts a spacer that may be used for repaired jaw alignment, typically when the subject or patient is missing teeth. In this particular case, maxillary teeth are absent, and as such, the spacer extends from the maxilla.

Regardless of the methodology used, the fractured shards are realigned into the normal position, as can be seen in FIG. 2C. At this point, if the subject or patient is missing or lacking any teeth, such that the maxilla or mandible would be over rotated if the anterior edges of the maxilla and mandible were approximated, a spacer (shown in FIG. 2D) can be positioned. FIG. 2D shows the subject or patient lacking maxillary teeth, and as such, the spacer is used to represent the maxillary teeth so that the mandible does not over rotate and thus lead to non-anatomic healing. In other words, the spacer is used to maintain the spacing that healthy dentition would otherwise occupy. It is contemplated herein that this spacer can be positioned on the mandible as well if the mandibular teeth are absent to prevent over rotation of the mandible.

Figure 2E:
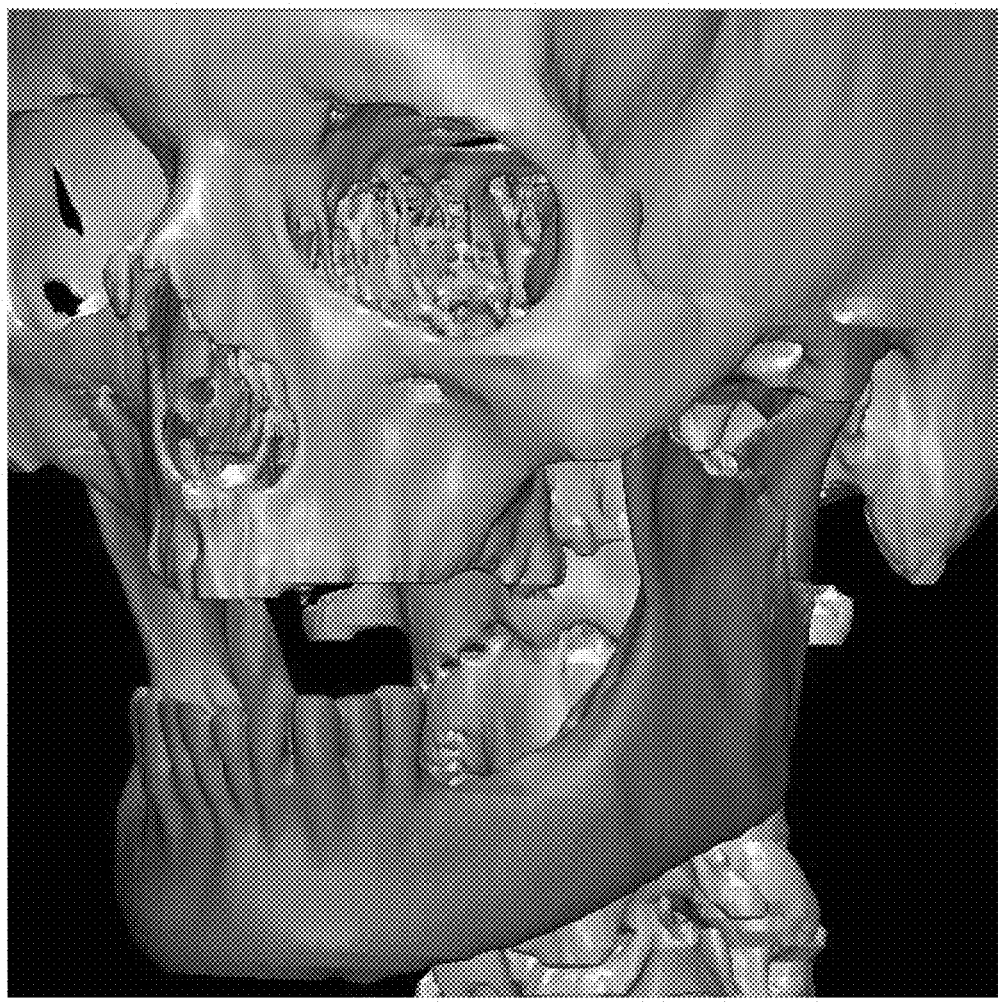
FIG. 2E depicts a realigned, repaired jaw from FIGS. 2A-2D.
Figure 2F:
FIG. 2F is a CT image of the realigned jaw (blue) compared to the original fractured jaw from FIG. 2A.

Once the fractured shards of the jaw are realigned, as seen in FIG. 2C, and any spacing issues are resolved (see FIG. 2D), the jaw of the subject or patient can be realigned and fixed, as in FIG. 2E. FIG. 2F shows a comparison of the realigned jaw (in blue) as compared to the underlying original position of the dentition. The jaw (and resulting splint) should be realigned, however, in order to provide proper healing and reduction of the fractures.

Figure 3A:
FIG. 3A depicts an initial blank creation from the U-shape that follows the top of the jaw line.
Figure 3B:
FIG. 3B depicts an initial blank creation from the U-shape that follows the middle of the jaw line.
Figure 3C:
FIG. 3C depicts an initial blank creation from the U-shape that follows the lower portion of the jaw line.
Figure 3D:
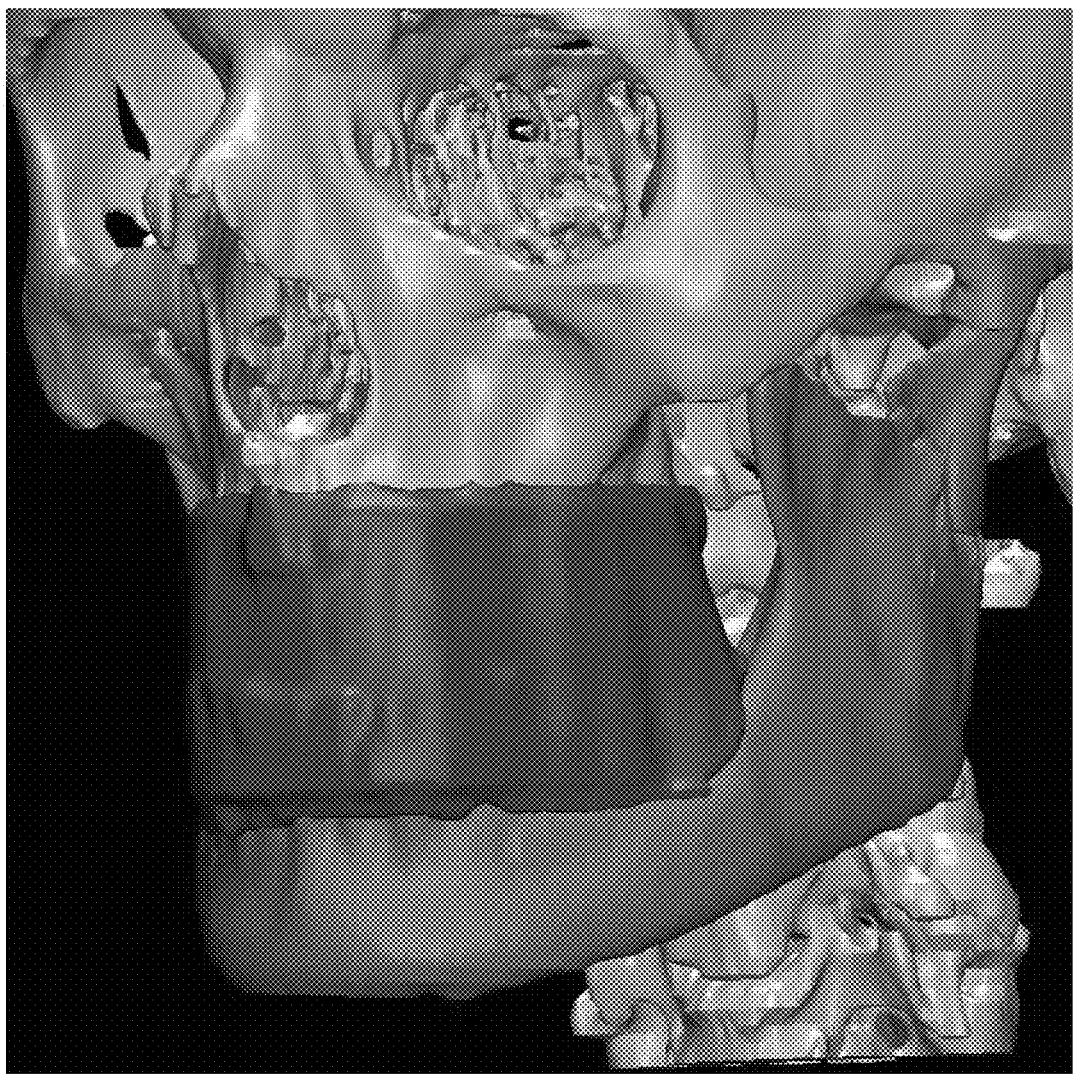
FIG. 3D is a 3D model/image/representation of the blank (initial splint configuration) resulting from interpolation of FIGS. 3A-3C.

At this point, a "blank" or initial splint configuration can be created on the image processing software program. Using the image of the subject or patient, various portions of the splint itself can begin taking form. The upper palate is lined, forming the uppermost portion of the splint, including the palate, as shown in FIG. 3A. A "U-shape" can then be drawn or illustrated along the upper (maxillary) jaw/dentition (FIG. 3B) and also along the lower (mandibular) jaw/dentition (FIG. 3C). These "U-shapes" follow the jaw line of the subject or patient. The distance between the results of FIGS. 3A-3C are then interpolated within the software program to create the general size of the blank or initial splint. The interpolation can be indicated in any way, such as by coloring in the distance as a solid, as can be seen in blue in FIG. 3D. Once this initial model is made, the stereolithic files (STL) can be imported into any suitable design software package, such as 3-MATIC by MATERIALISE.

Figure 4:
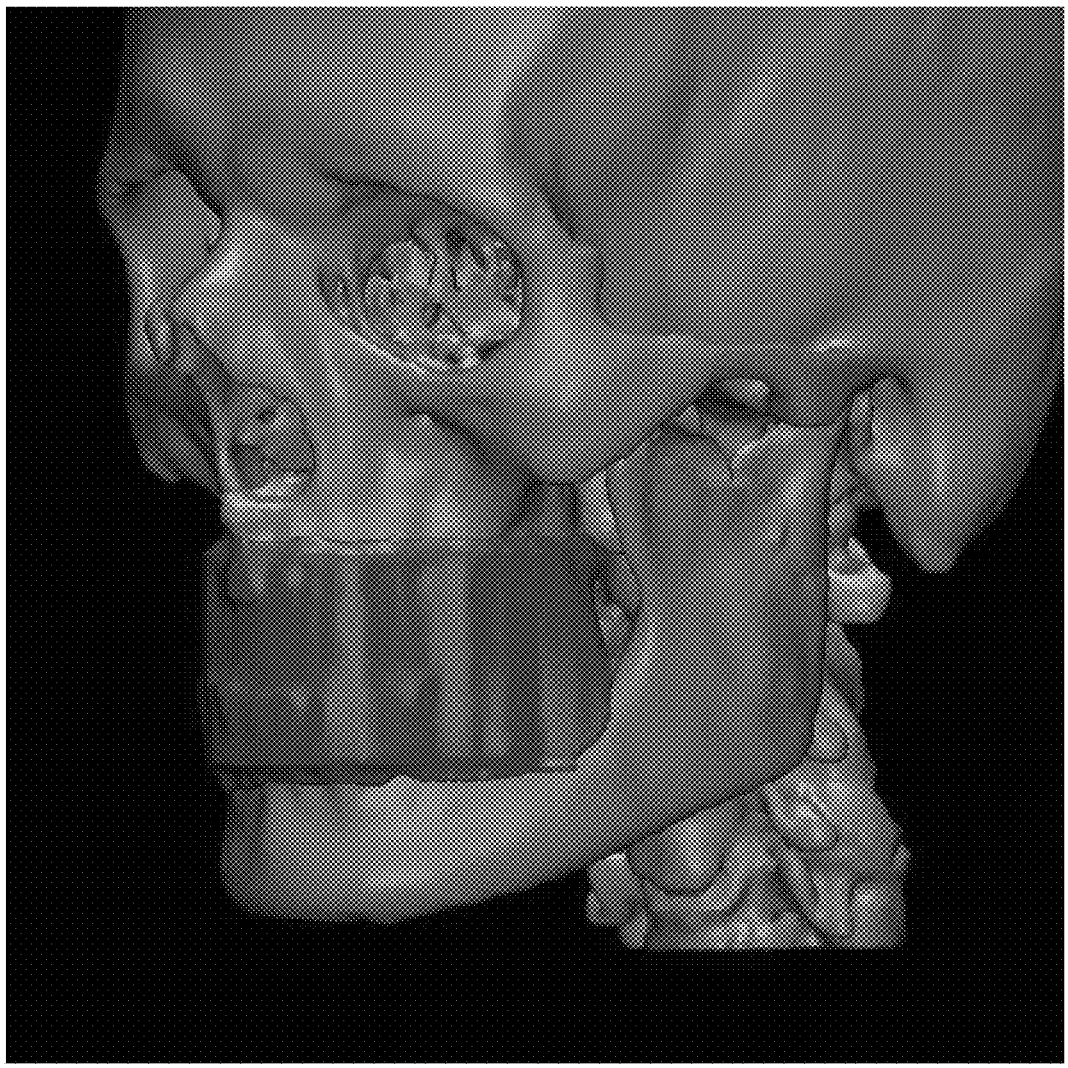
FIG. 4 depicts expansion of the dentition and bone to create space between the blank and the dentition/bone.

From there, the boney and dental three-dimensional (3D) anatomy can be wrapped with a 1-mm detail parameter and/or a "protect thin walls" parameter (e.g., setting that slightly expands the bone, for example 0.5-0.8 mm from its original thickness) to de-feature and slightly expand the bone, as seen in FIG. 4, which, in turn, slightly expands the splint to account for variability and for the subject or patient's gums, and so that the dentition can fit within the splint comfortably but snugly. The purpose of this expansion can be seen most clearly in FIG. 13E, where the splint covers the outside of the subject or patient's dentition. The expansion typically is relatively small, for example between about 1.24 mm and about 2 mm.

Figure 5A:
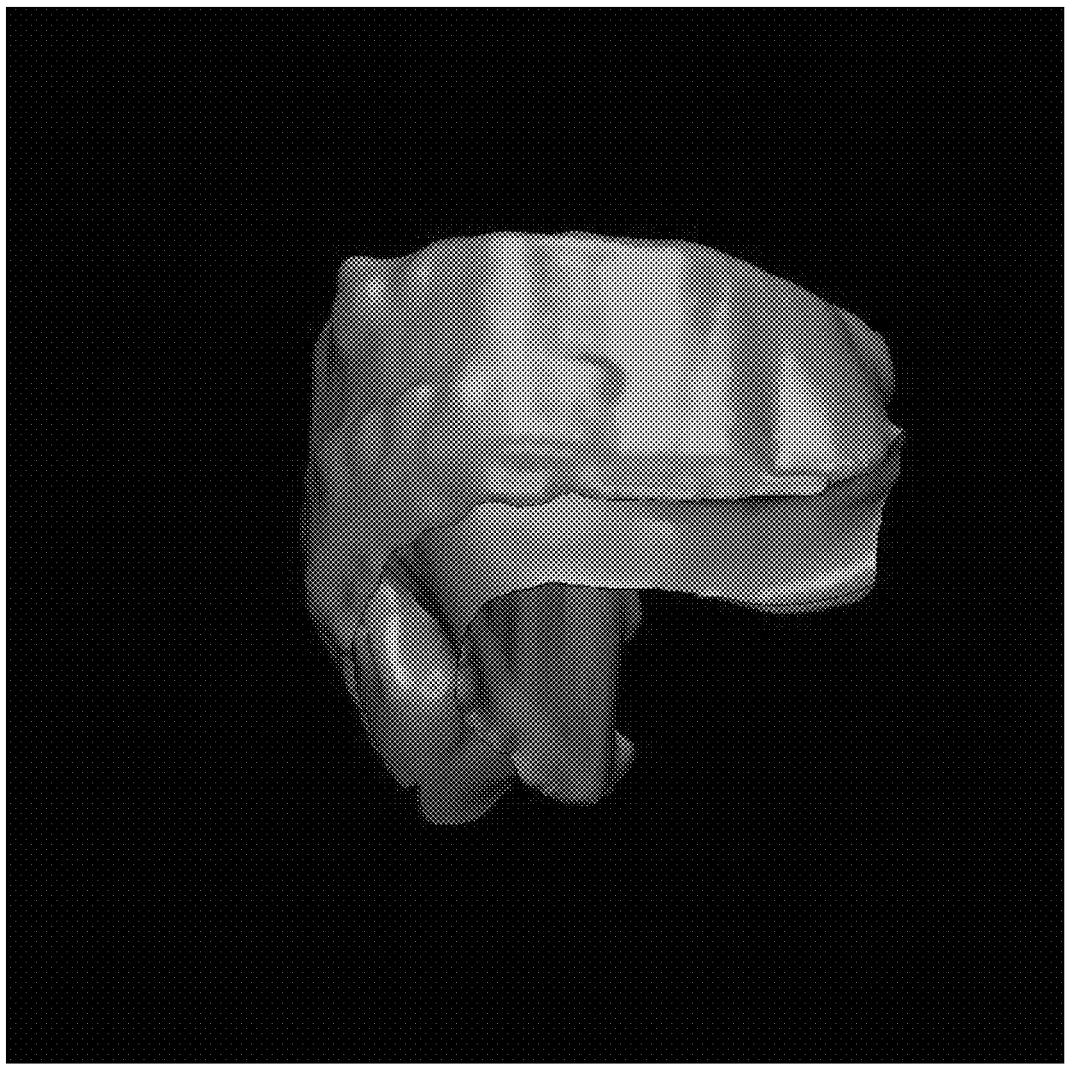
FIG. 5A is a lower perspective view of the blank (initial splint configuration) upon removal of the bone and dentition on the image processing software program.
Figure 5B:
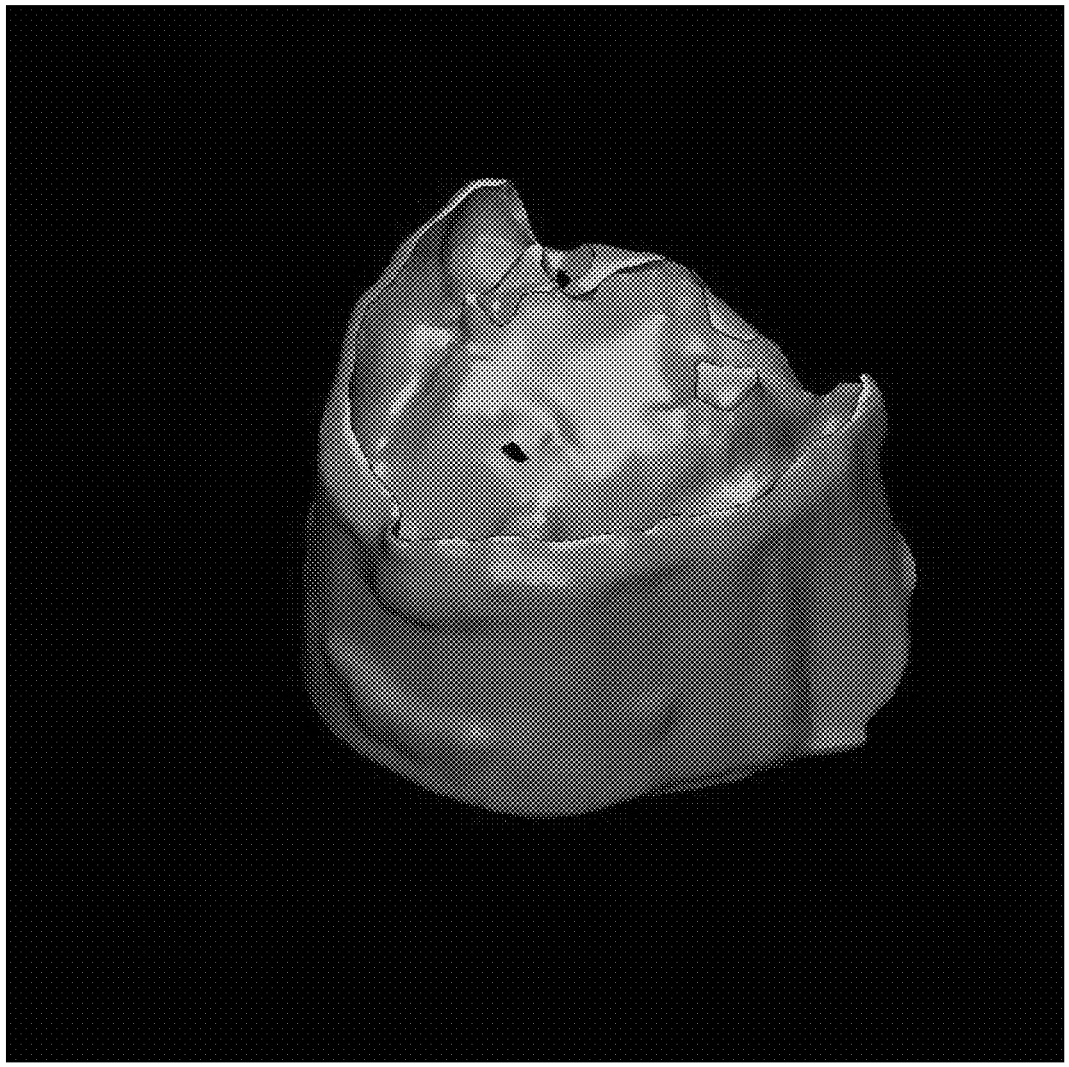
FIG. 5B is an upper perspective view of the blank (initial splint configuration) of FIG. 5A.

Using a Boolean subtraction or other suitable methodology, the bone and any dentition is subtracted from the splint, leaving only an image of the initial splint configuration, as can be seen in FIGS. 5A-5B. The distances of the splint can then be checked and altered to ensure that the lip and tongue frenula are not impacted.

Figure 6:
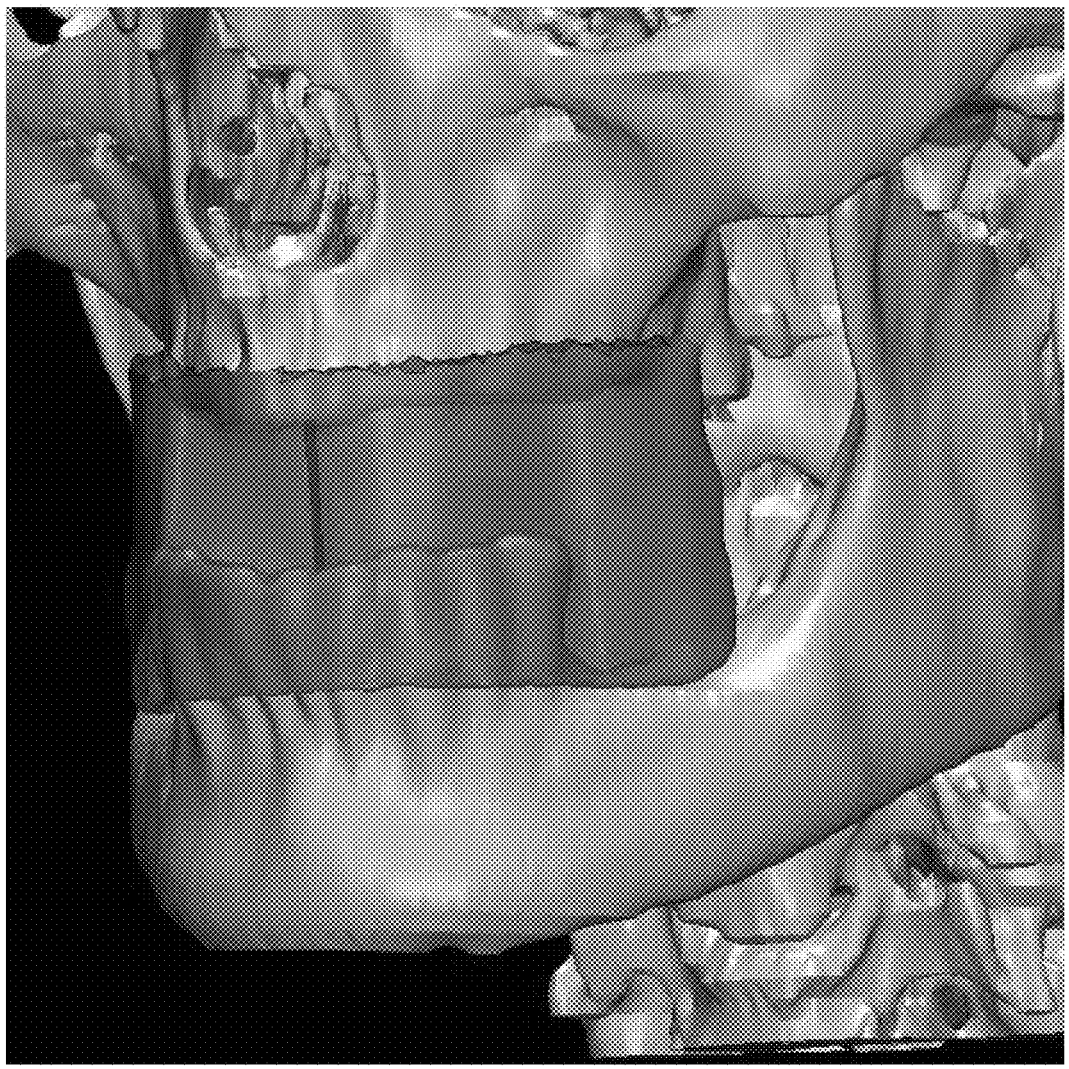
FIG. 6 depicts the initial splint configuration upon trimming for better fit on the subject or patient.

The top and/or bottom edges of the initial splint configuration may be trimmed, as the splint (FIGS. 5A-5B) formed from the interpolation of FIGS. 3A-3C may be oversized or include an excessive amount of the oral cavity. As such, it can be trimmed for better fit for the subject or patient, as seen in FIG. 6.

At this point, i.e., upon creation of the image of the initial splint configuration (optionally trimmed for fit, if needed) by itself, the following steps do not necessarily need to be performed in the order presented herein. Any order may be used, as determined by one of ordinary skill in the art, to form the resulting oral splint.

Figure 7A:
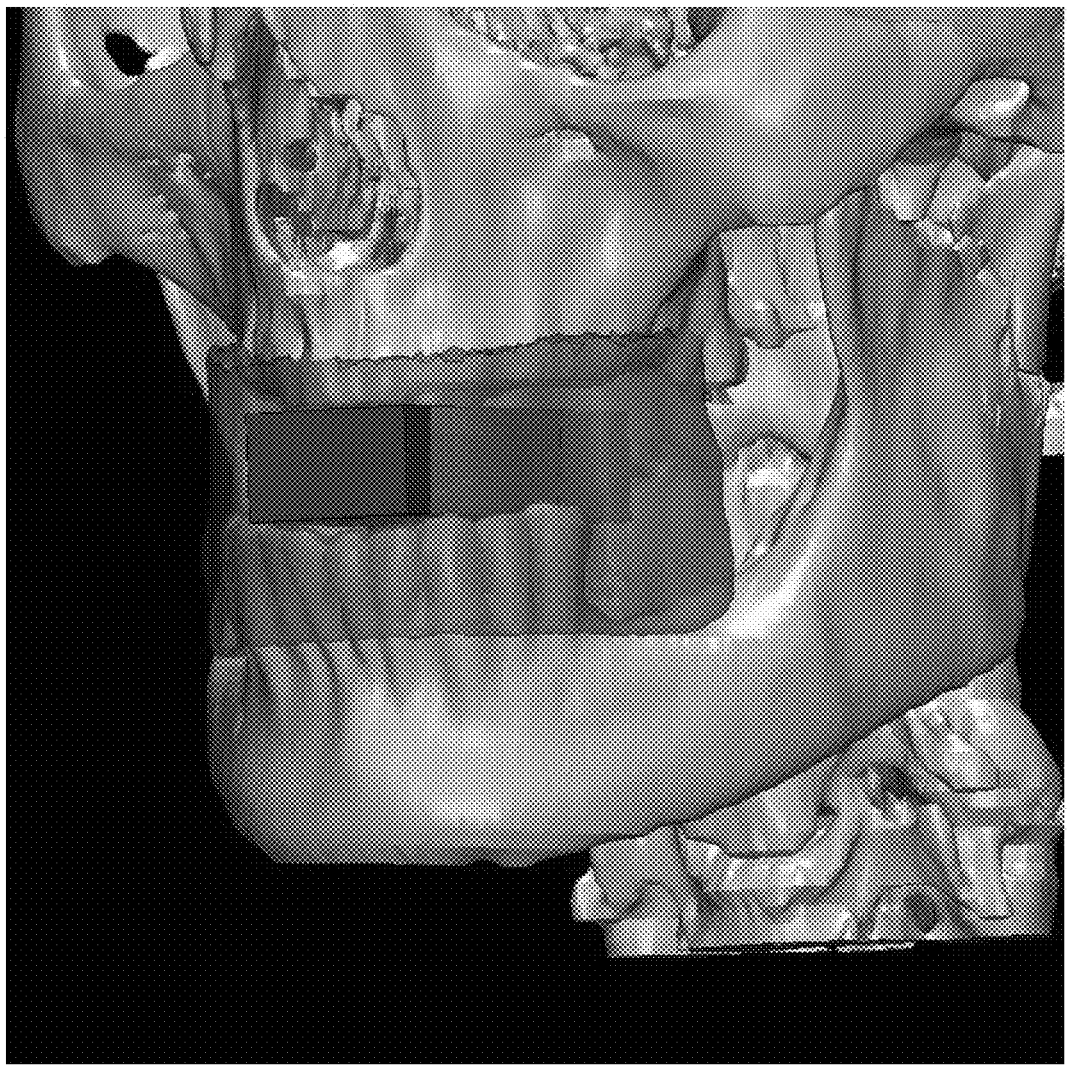
FIG. 7A depicts a rectangular block inserted into the anterior portion/end of the initial splint configuration. Although a rectangular shape is shown herein, any suitable shape (e.g., circular/cylindrical, triangular, asymmetrical or amorphous, etc.) is contemplated herein by the current invention.
Figure 7B:
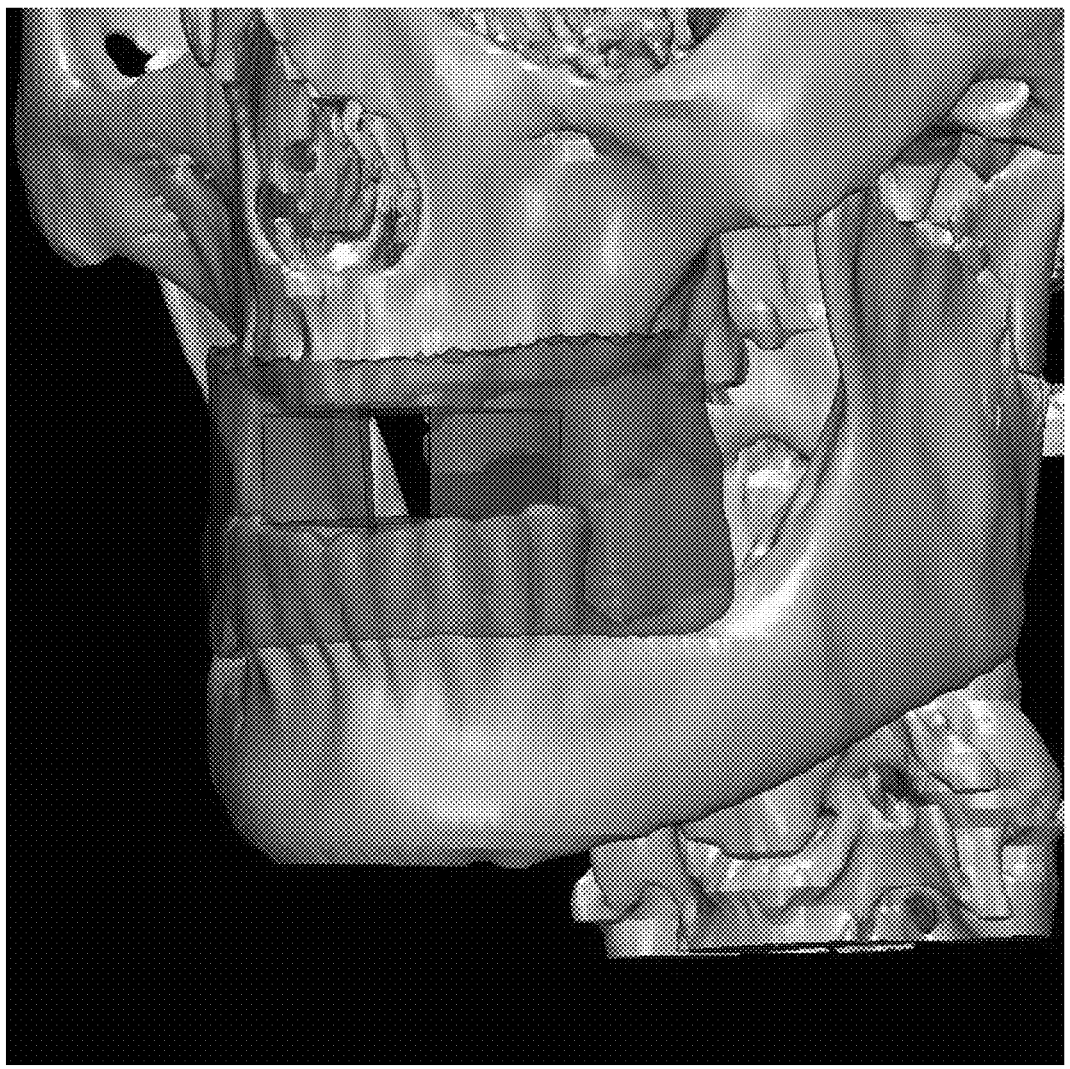
FIG. 7B depicts creation of the evacuation aperture via removal of the block of FIG. 7A.

FIGS. 7A-7B depict formation of an evacuation aperture within an anterior portion/end of the initial splint on the image processing software program. A rectangular block is inserted through the anterior end of the initial splint. Any shape of this block is contemplated herein. When the block is removed, an aperture is formed, as in FIG. 7B. The aperture can be of any suitable size, for example having a 12-mm height and a 20-mm width. The aperture is formed in the anterior portion of the splint to accommodate the suctioning instrumentation or similar device that allows evacuation of oral or gastric contents from the patient as needed, thus preventing aspiration. It is contemplated herein that the aperture can be of any suitable shape and size or may be removed from the design entirely, depending on the needs of the patient.

Figure 8A:
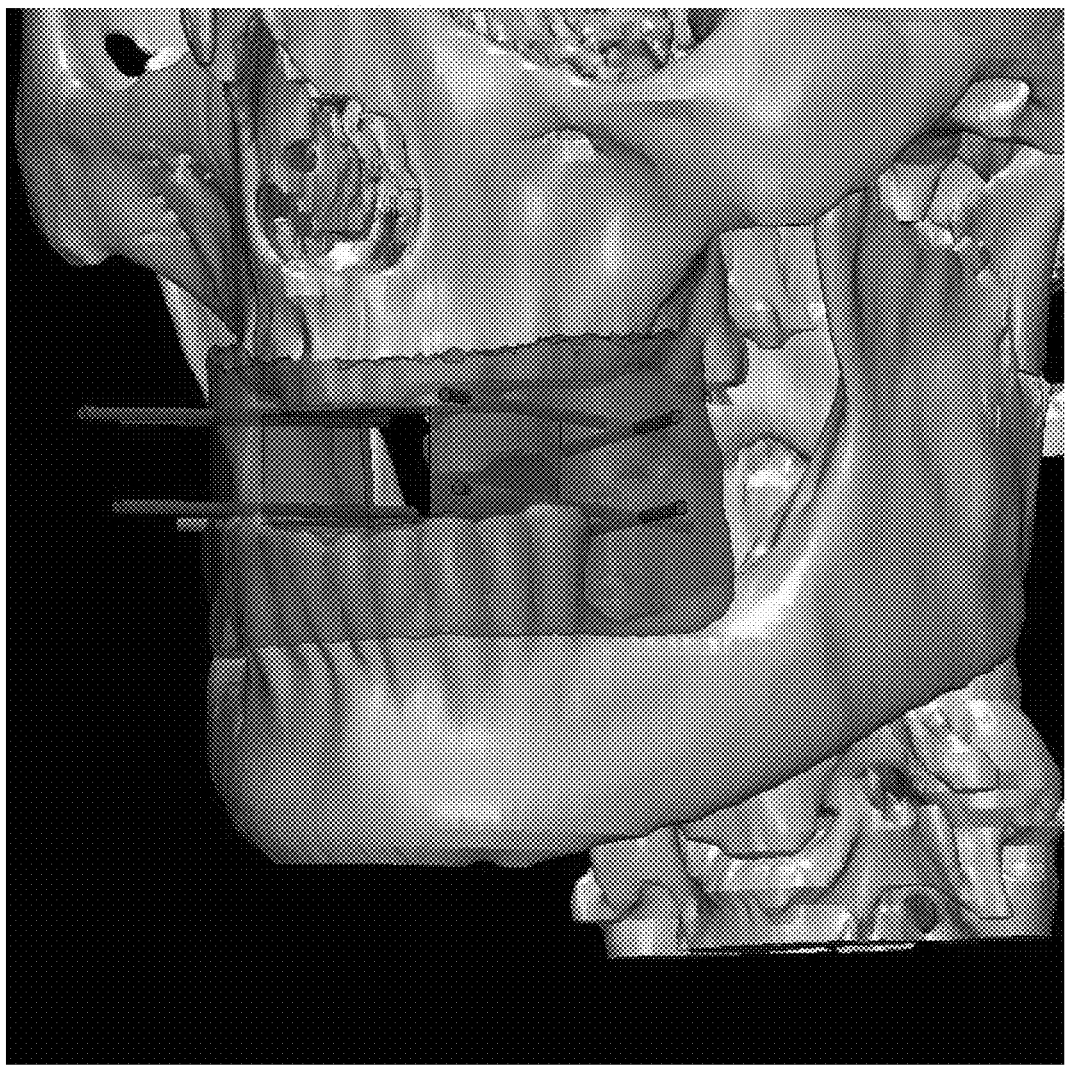
FIG. 8A depicts cylindrical insertions inserted into an anterior side of the initial splint configuration. Although a cylindrical shape is shown herein, any suitable shape (e.g., rectangular, triangular, asymmetrical or amorphous, etc.) is contemplated herein by the current invention.
Figure 8B:
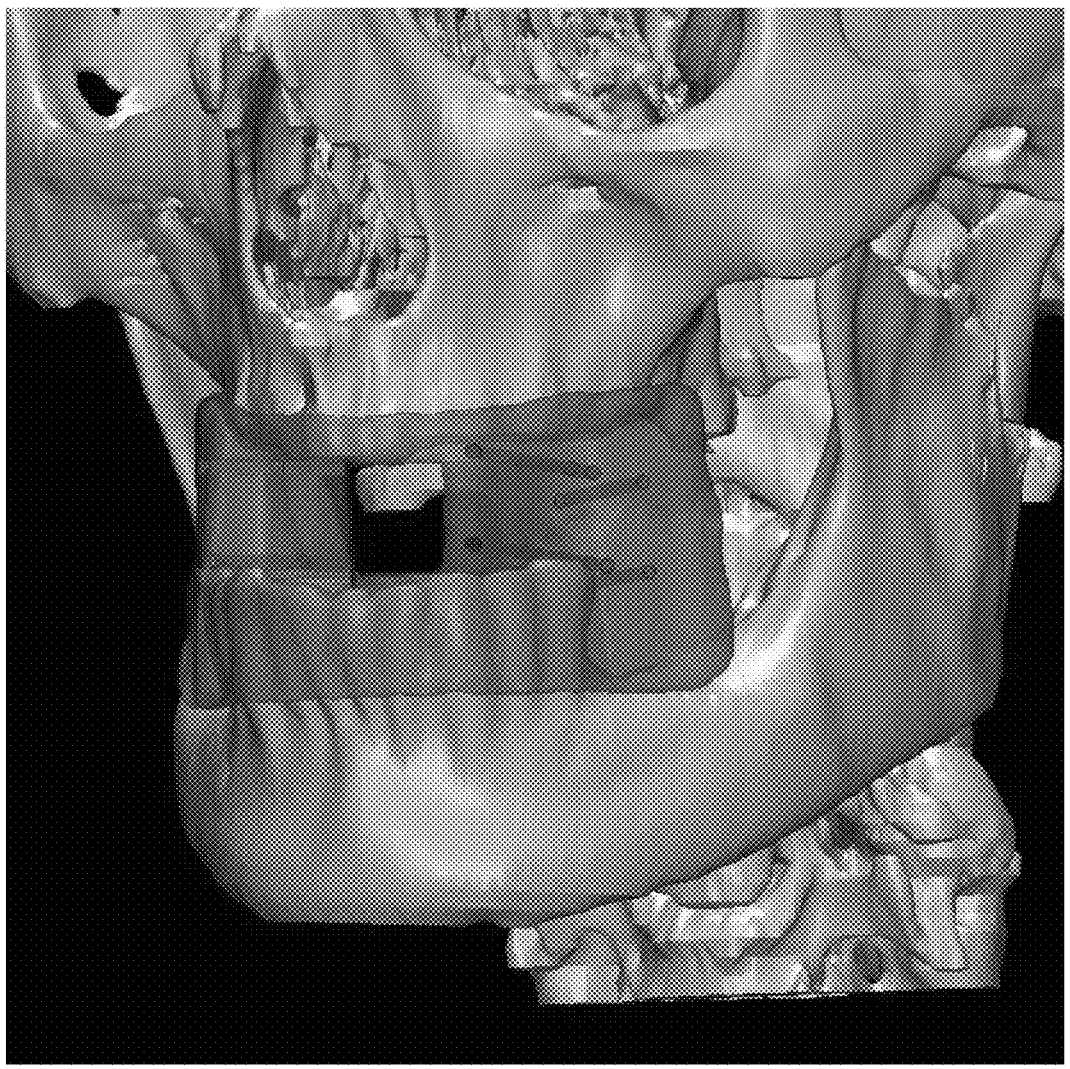
FIG. 8B depicts creation of the guide wire apertures via removal of the insertions of FIG. 8A.

FIGS. 8A-8B depict formation of guide wire apertures within an interior portion of the initial splint on the image processing software program. Cylindrical blocks are inserted through the anterior portion of the initial splint. When the cylindrical blocks are removed, a plurality of small apertures are formed, as in FIG. 8B. It is contemplated herein that there can be any number (e.g., eight) of apertures at any suitable size (e.g., 1.5 mm diameter) and with any suitable shape. Each aperture in the upper half of the initial splint, however, should have a corresponding aperture in the lower half of the initial splint, or vice versa. For example, there may be four (4) apertures in the upper half of the initial splint, and four (4) corresponding apertures in the lower half of the initial splint. These smaller apertures accommodate for wiring. These apertures would be used during installation of each of the maxillary and mandibular splints in order to secure the maxillary splint to the patient's maxilla and secure the mandibular splint to the patient's mandible. This will become clearer as this specification continues.

Figure 9A:
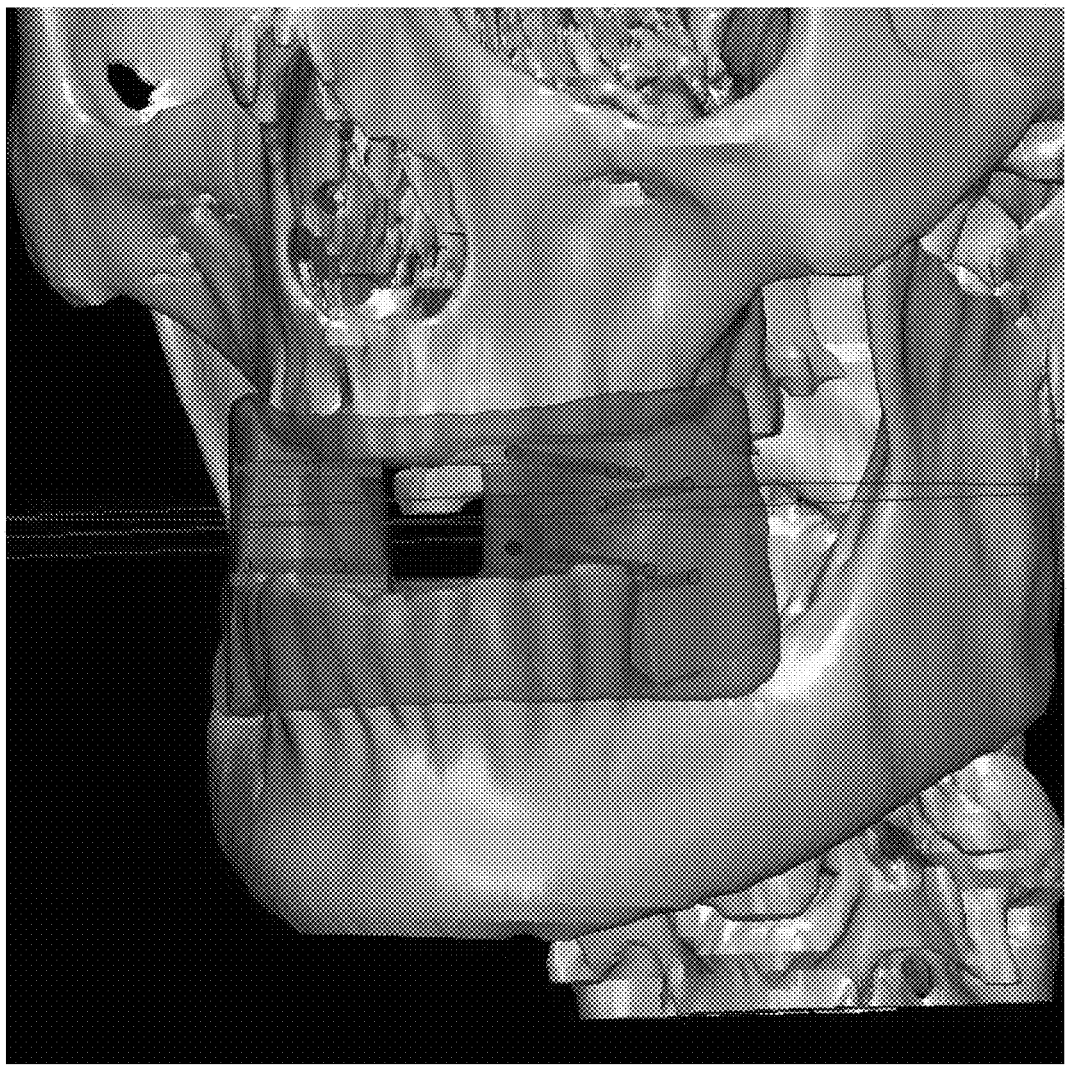
FIG. 9A depicts creation of a cutting plane for splitting the initial splint configuration into an upper (ultimately, maxillary) splint and a lower (ultimately, mandibular) splint.
Figure 9B:
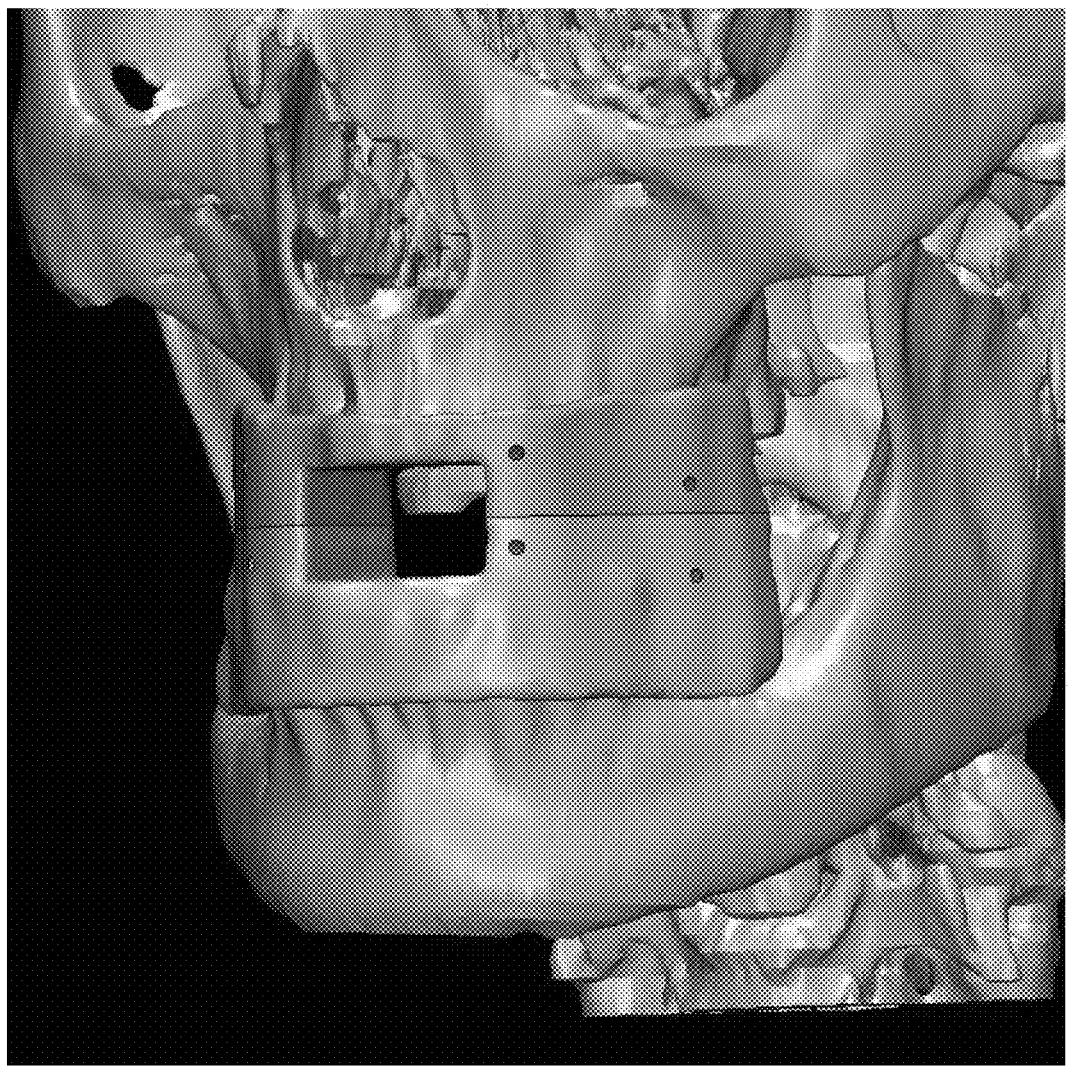
FIG. 9B depicts the splint upon being split by the plane of FIG. 9A.

FIGS. 9A-9B depict splitting of the initial splint into an upper portion (forming the maxillary splint) and a lower portion (forming the mandibular splint). This can be accomplished in any suitable manner. For example, as can be seen in FIG. 9A, an anterior-posterior (horizontal) plane is created somewhere along the midsection of the initial splint to slice the splint into an upper/superior portion, which becomes the maxillary splint, and a lower/inferior portion, which becomes the mandibular splint.

Figure 9C:
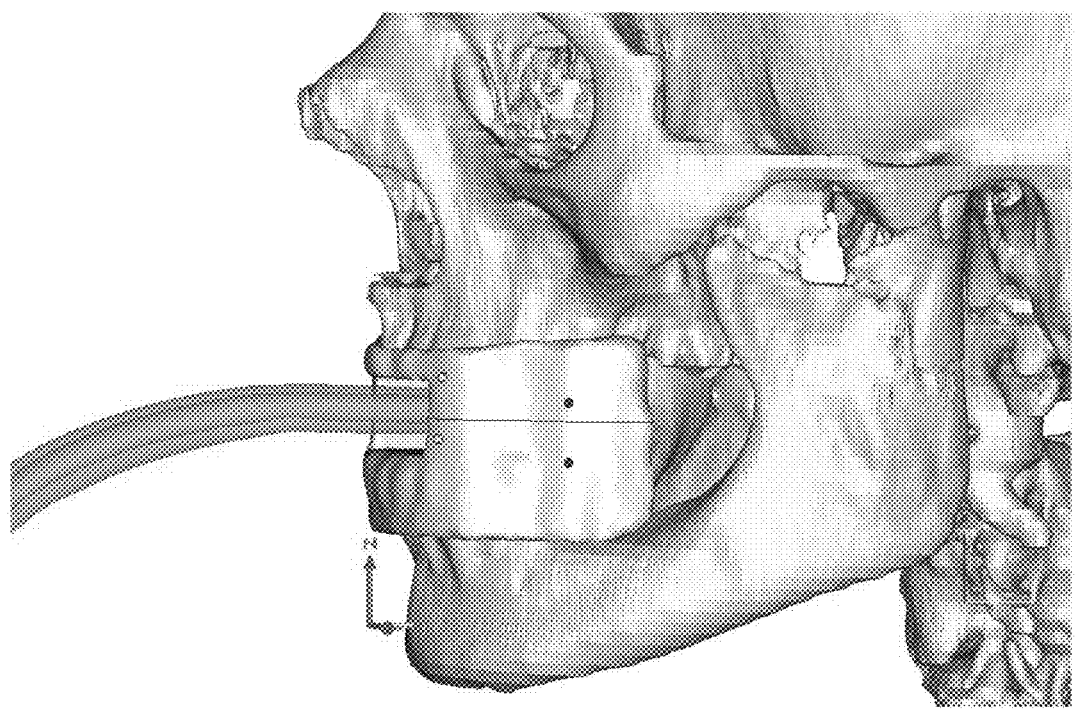
FIG. 9C depicts the split splint with suctioning instrumentation positioned through the evacuation aperture formed in FIG. 8B.

The location of where this plane is created along the midsection of the splint is determined by the number and size of the patient's teeth along his/her maxilla and mandible. For example, if the patient's upper teeth and lower teeth are all present and similarly sized, the plane can be created substantially in the middle of the midsection to create two (2) halves. However, if, for example, the patient is missing his/her upper/maxillary teeth, then the plane would be created closer to the upper gum line of the patient. FIGS. 9B-9C show this particular example, where the upper portion/maxillary splint can be seen to be shorter in height vertically than the lower portion/mandibular splint. In this particular case, the patient was missing a majority of his/her upper/maxillary teeth. Based on this concept, one of ordinary skill in the art would be able to determine different locations of the plane for slicing or splitting the splint into the upper and lower portions.

FIG. 9B shows the splint after having been split into its upper and lower portions, for example by the anterior-posterior plane of FIG. 9A. FIG. 9C shows the split splint with suctioning instrumentation inserted through the evacuation aperture formed in FIG. 8B.

Figure 10A:
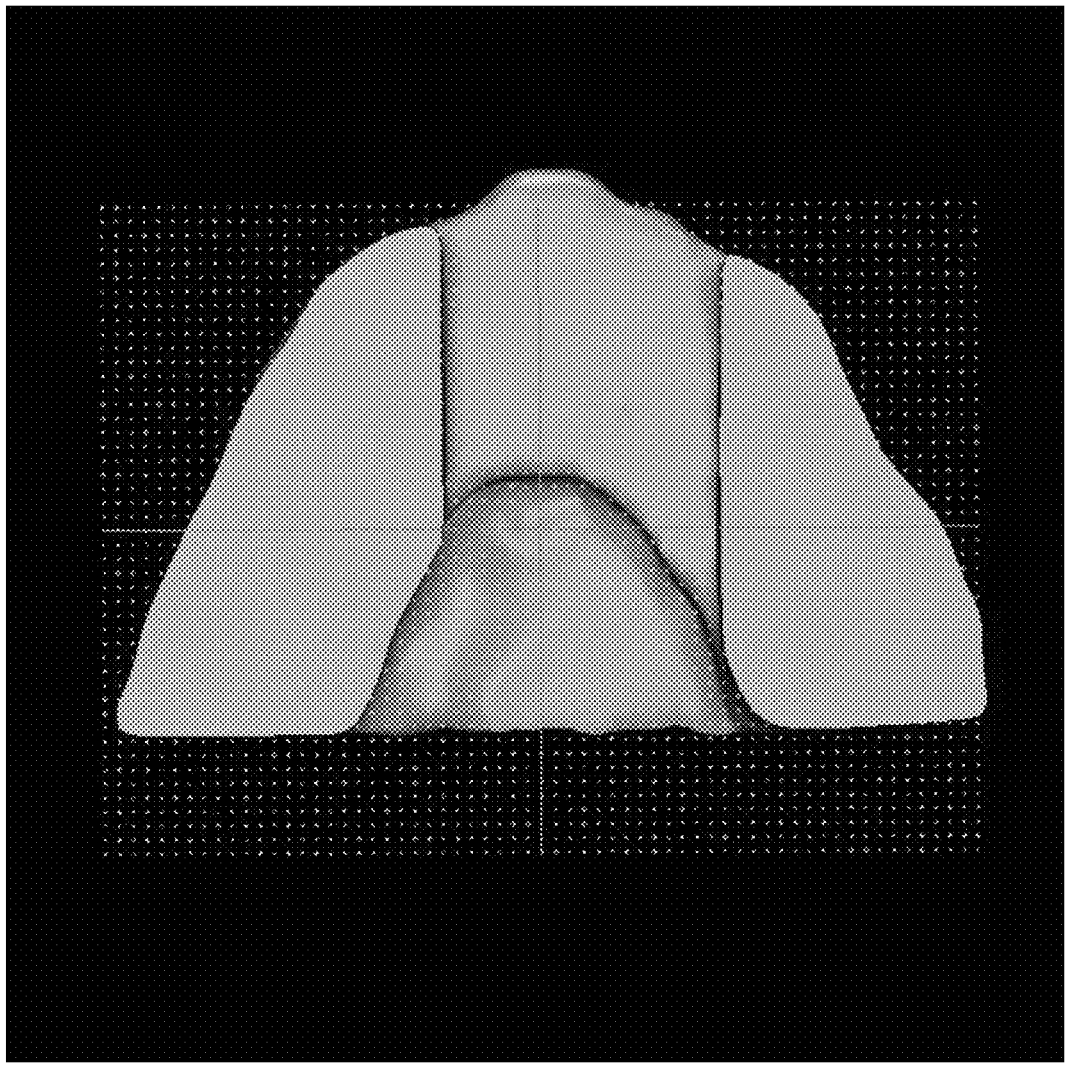
FIG. 10A depicts a sketch plane for creation of structures on the upper and lower splints that facilitate stability and securement of the upper and lower splints when coupled together.

The upper portion of the splint, which becomes the maxillary splint, has a superior/upper side/surface and an inferior/lower side/surface; similarly, the lower portion of the splint, which becomes the mandibular splint, also has a superior/upper side/surface and an inferior/lower side/surface. Structures for stabilizing the upper portion of the splint and the lower portion of the splint together when the splint is "closed" (i.e., when the inferior surface of the upper splint is contacting the superior surface of the lower splint) may be positioned on the inferior surface of the upper splint and the superior surface of the lower splint, respectively. FIG. 10A shows a sketch plane on the inferior surface of the upper splint. The sketch plane is used for drawing out the structure(s) to be placed on the inferior surface of the upper splint, where the structure(s) facilitates stability and securement of the upper and lower splints when coupled together. It can be appreciated that this sketch plane can be used with any surface/side of any of portion of the splint to draw any structure needed.

Figure 10B:
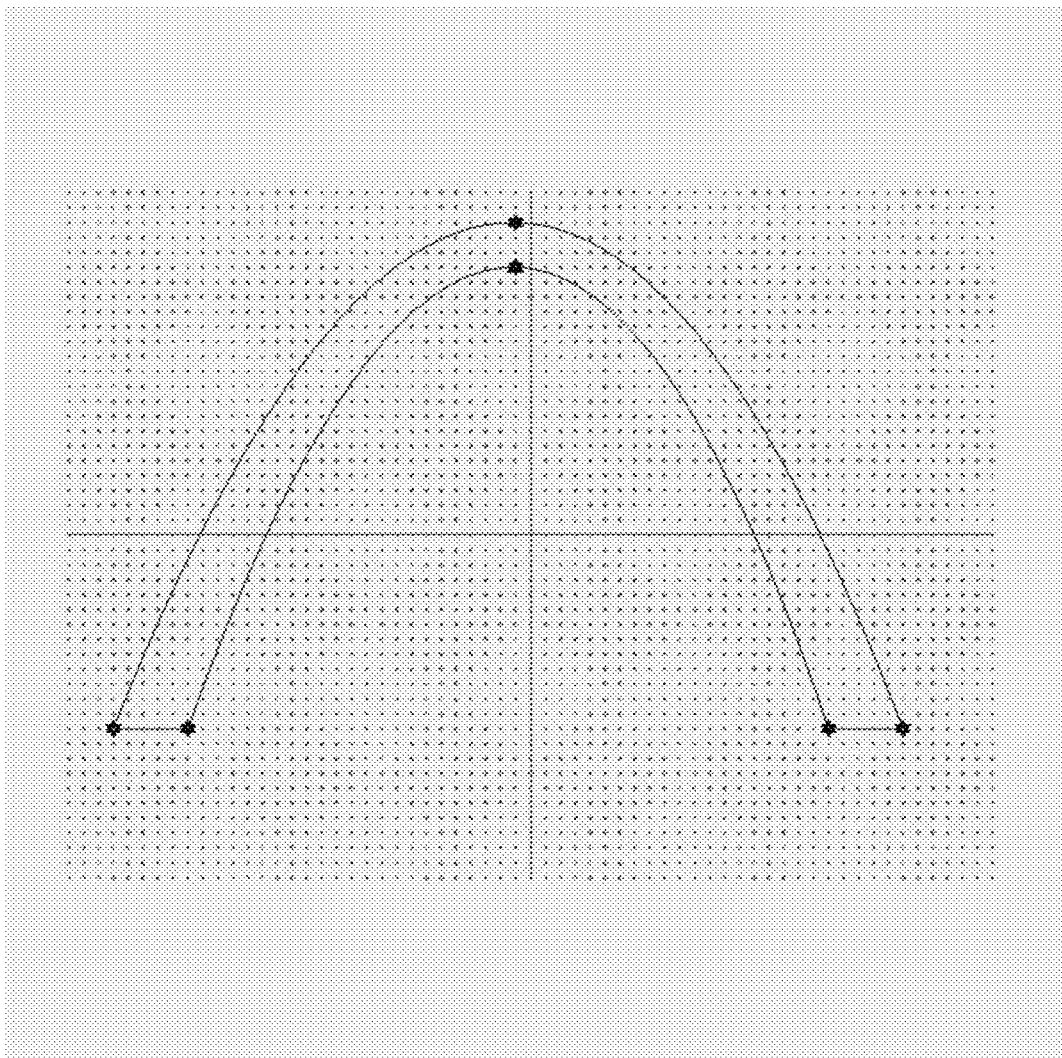
FIG. 10B depicts a drawing of a tongue-and-groove mechanism on the sketch plane of FIG. 10A.
Figure 10C:
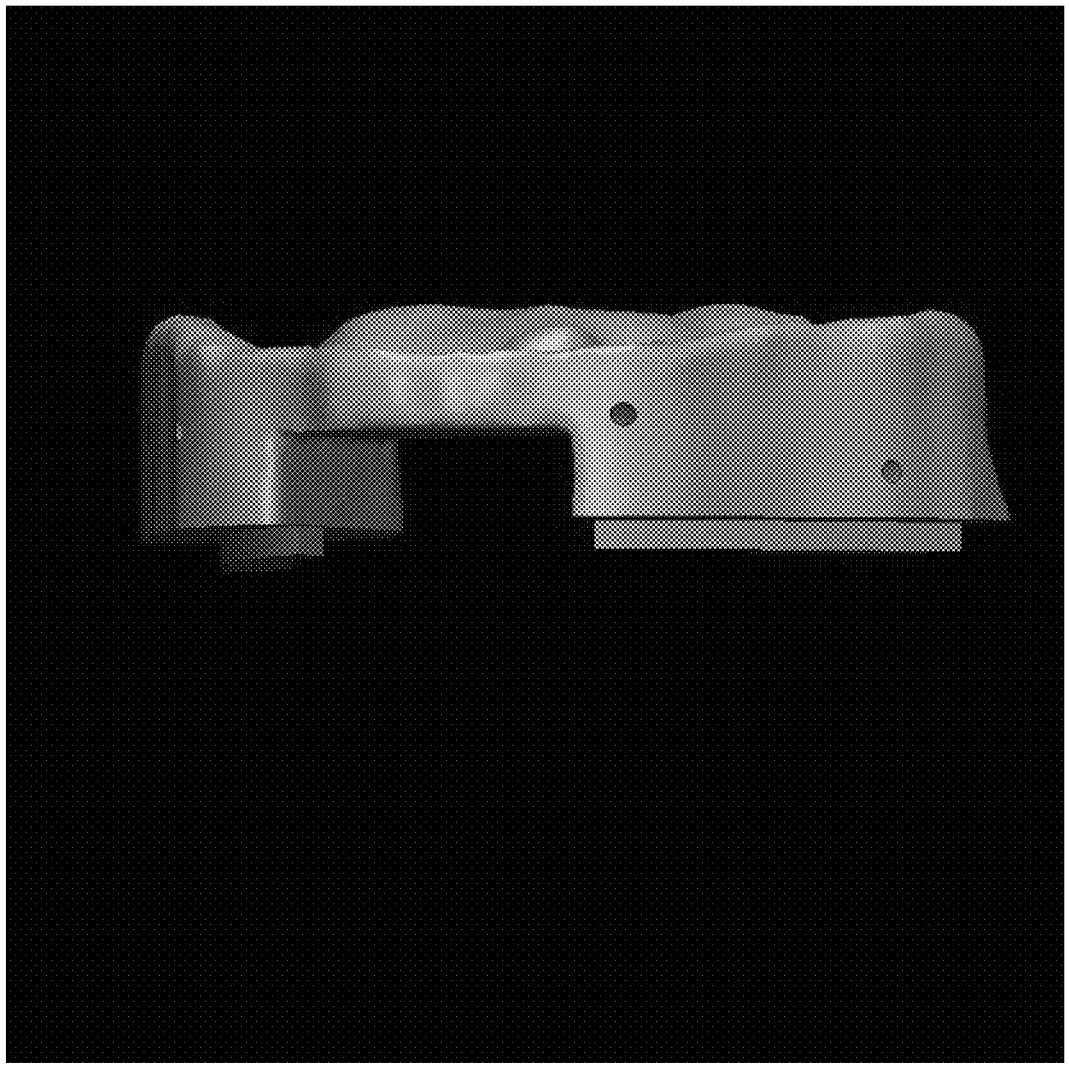
FIG. 10C depicts formation and extrusion of a tongue structure along the upper splint, based on the drawing of FIG. 10B. It is contemplated herein that the tongue structure can be positioned on either the upper splint or the lower splint.

An exemplary mechanism for stabilizing the upper and lower portions of the splint when contacting each other is a tongue-and-groove fitting, which is described herein, though any suitable mechanism is contemplated by the current invention. FIG. 10B shows a U-shaped drawing of the tongue portion of the fitting on the sketch plane of FIG. 10A, resulting in the tongue portion being disposed on the inferior surface of the upper splint, as seen in FIG. 10C. It can be appreciated that the sketch plane and U-shaped drawing could have been positioned on the superior surface of the lower splint, rather than on the inferior surface of the upper splint as in FIGS. 10A-10C; this would result in the tongue portion being disposed on the superior surface of the lower splint. The U-shaped sketch creates an extruded surface (e.g., 2 mm in height), as can be seen in FIG. 10C (and also FIG. 12B where the extruded surface is seen on the superior surface of the lower splint).

Figure 10D:
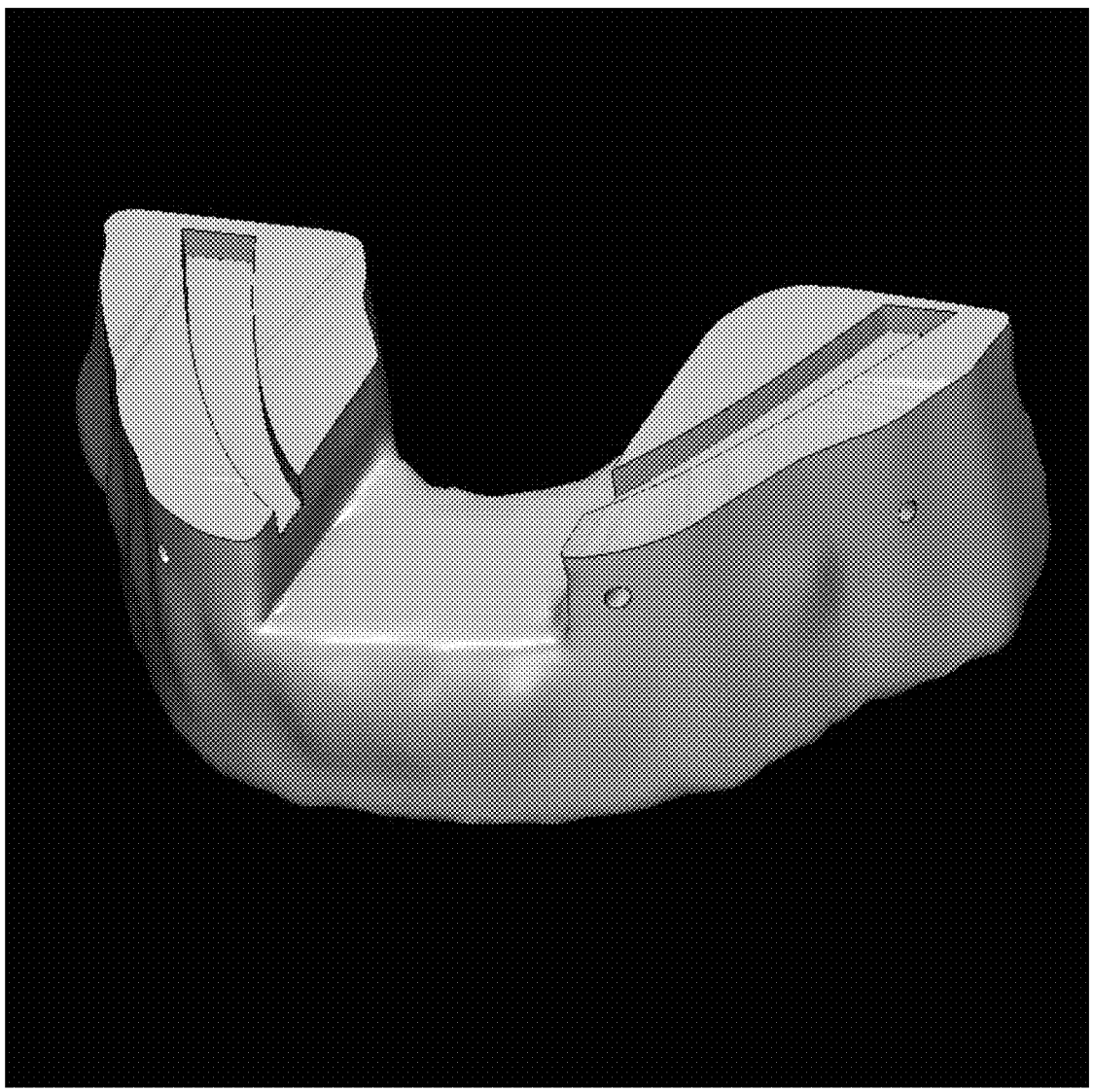
FIG. 10D depicts subtraction and formation of a matching groove structure along the lower splint, positioned opposite from the tongue structure of FIG. 10C. It is contemplated herein that the groove structure can be positioned on either the upper splint or the lower splint, just opposite from where the tongue structure was formed.

In either case, this extruded surface (i.e., tongue portion) is then Boolean or otherwise subtracted from the opposite surface on the opposite portion of the splint. For example, if the extruded surface is created on the inferior surface of the upper (maxillary) portion of the splint, as can be seen in FIG. 10C, then that extruded surface would be subtracted from the superior surface of the lower (mandibular) portion of the splint, as can be seen in FIG. 10D. On the other hand, if the extruded surface is created on the superior surface of the lower (mandibular) portion of the splint (see FIGS. 12B-12C), then that extruded surface would be subtracted from the inferior surface of the upper (maxillary) portion of the splint (see FIGS. 12D-12E). In either case, though, the extruded surface forms the tongue portion of the fitting, and the opposing subtraction forms the groove portion of the fitting, thus creating a tongue-and-groove fitting/mechanism between the upper and lower splints.

FIGS. 11A-11E depict fabrication of projections on the anterior face/surface of the upper and lower splints, where the projections facilitate the upper and lower splints being secured to one another stably. FIG. 11F depicts use of an example of these securement projections by lassoing or wrapping with intersplint wires. This will become clearer as this specification continues.

Figure 11A:
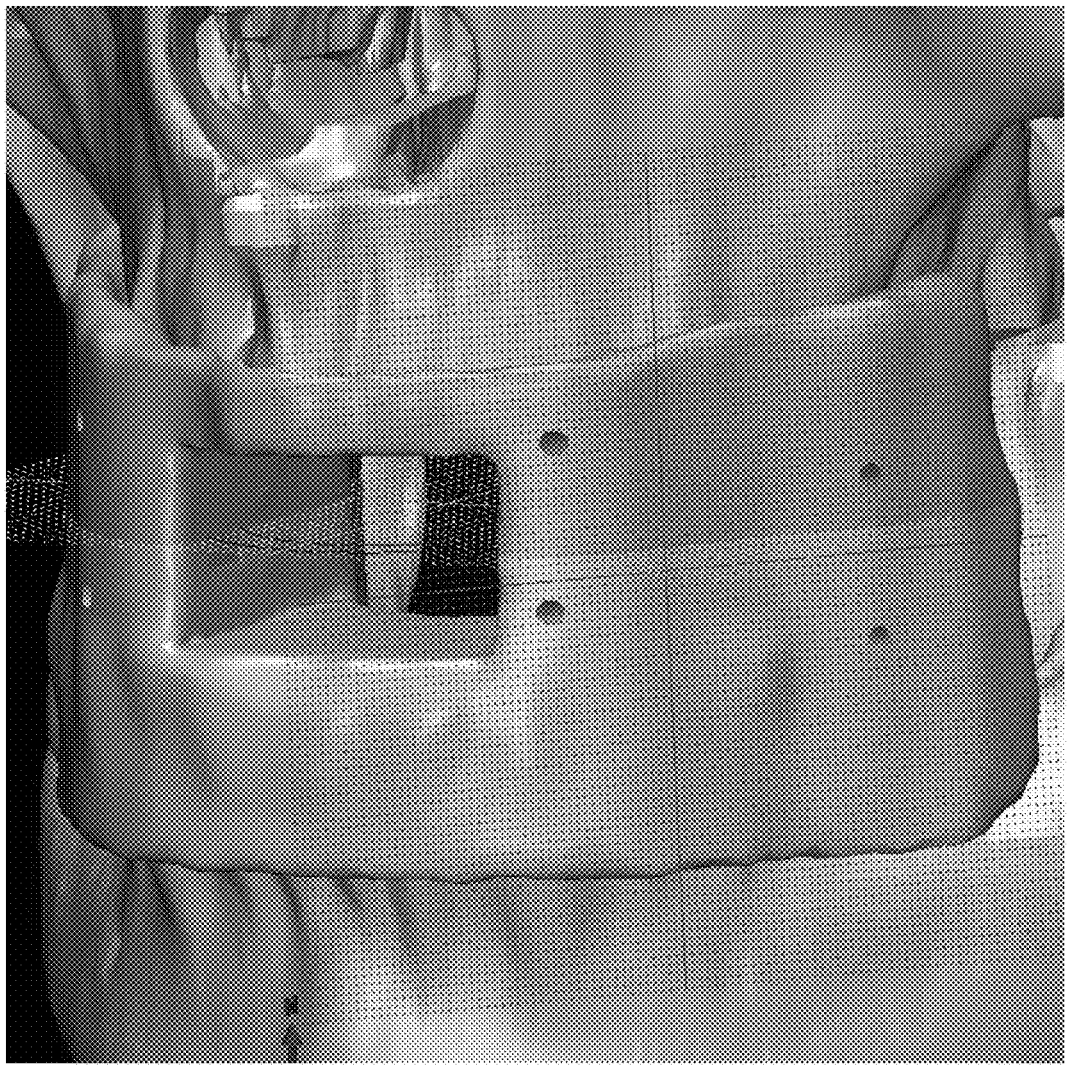
FIG. 11A depicts a sketch plane for creation of structures on the upper and lower splints that facilitate stability and securement of the upper and lower splints when coupled together.

FIG. 11A shows a sketch plane on the anterior surface of the splint. The sketch plane is used for drawing out the structure(s) to be placed on the anterior surface of the splint, where the structure(s) facilitates securement of the upper and lower splints when coupled together. It can be appreciated that this sketch plane can be used with any surface/side of any of portion of the splint to draw any structure needed. These structures typically are projections can be positioned on each of the upper (maxillary) and lower (mandibular) splints along the anterior surface of the splints. For example, a projection (e.g., a stud) can be positioned on each side of the evacuation aperture that was created in FIGS. 8A-8B. In this case, the projection can be any shape or form on the maxillary splint on each side of the evacuation aperture and also on the mandibular splint on each side of the evacuation aperture. The projections on each side of the evacuation aperture should align with each other from the maxillary splint to the mandibular splint, so that intersplint wires can be lassoed or tied around them to secure the maxillary and mandibular splints together.

Figure 11B:
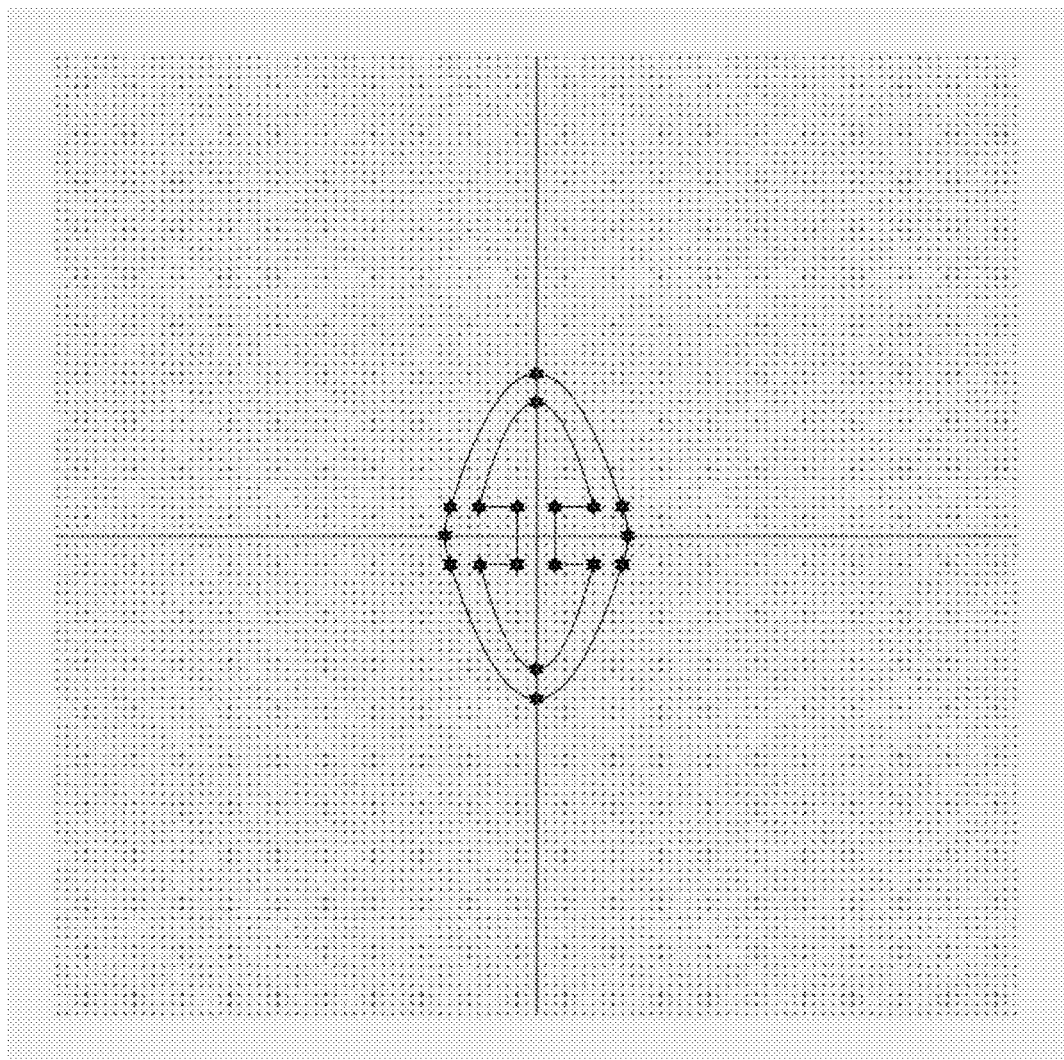
FIG. 11B depicts a drawing of an oval-shaped projection on the sketch plane of FIG. 11A. Although an oval-shaped projection is shown herein, any suitable shape or structure (e.g., studs, rectangular, etc.) is contemplated herein by the current invention, as long the structure(s) positioned on the upper and lower splints facilitates stability and securement of the upper and lower splints when coupled together.
Figure 11C:
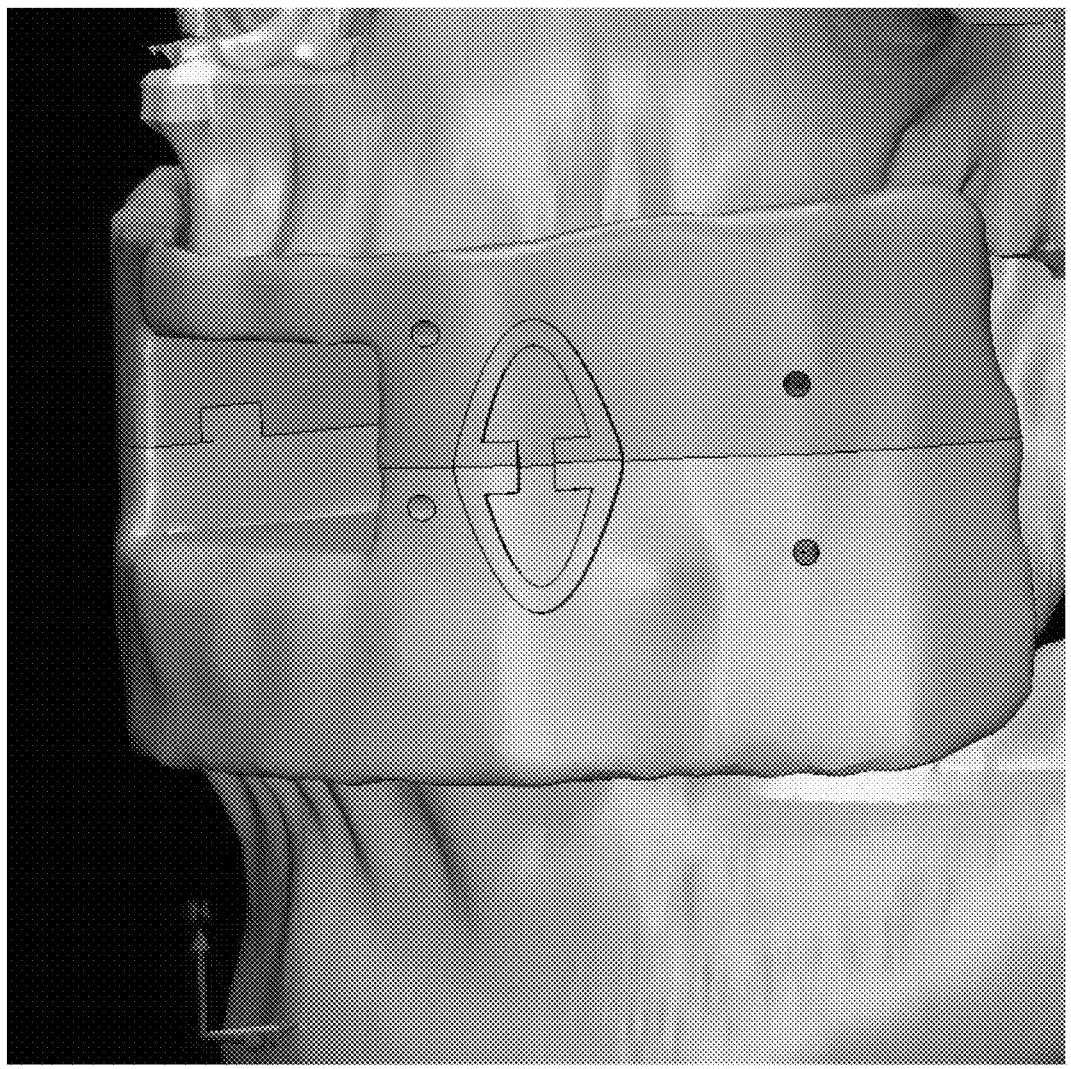
FIG. 11C depicts formation and extrusion of the oval-shaped projection on the upper and lower splints, based on the drawing of FIG. 11B, where an upper/superior portion of the oval-shaped projection is positioned on the upper splint and a lower/inferior portion of the oval-shaped projection is positioned on the lower splint.
Figure 11D:
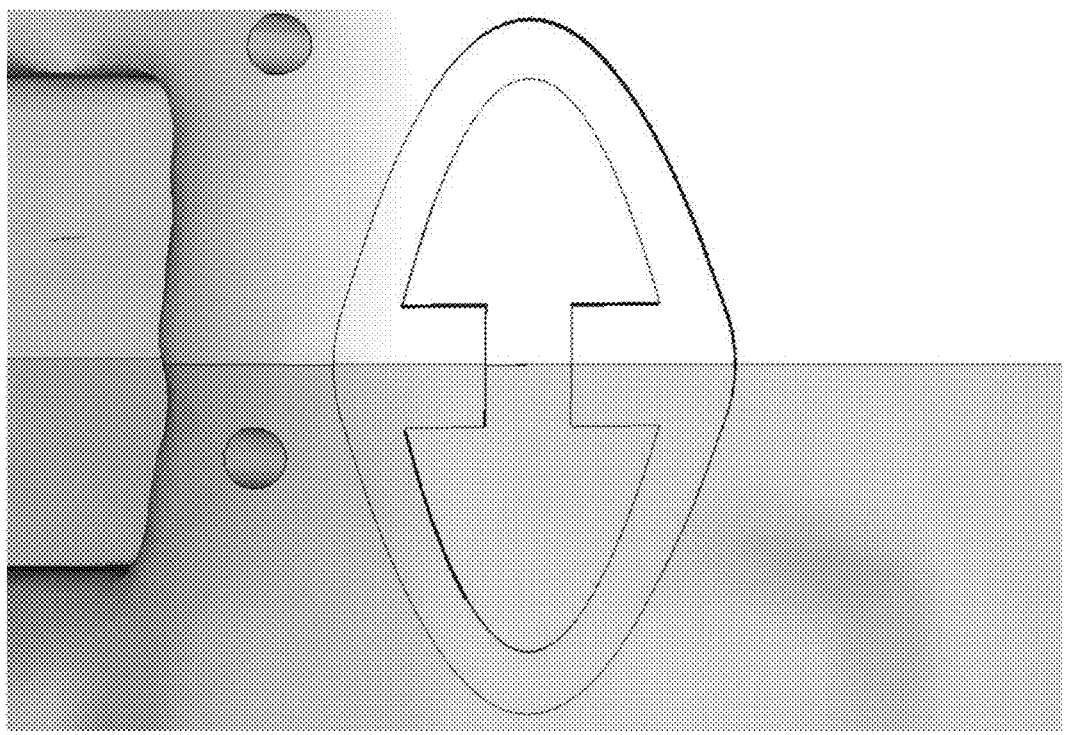
FIG. 11D is a close-up view of the projection of FIG. 11C. Typically, the projection is mirrored on the opposite side of the splint as well.
Figure 11E:
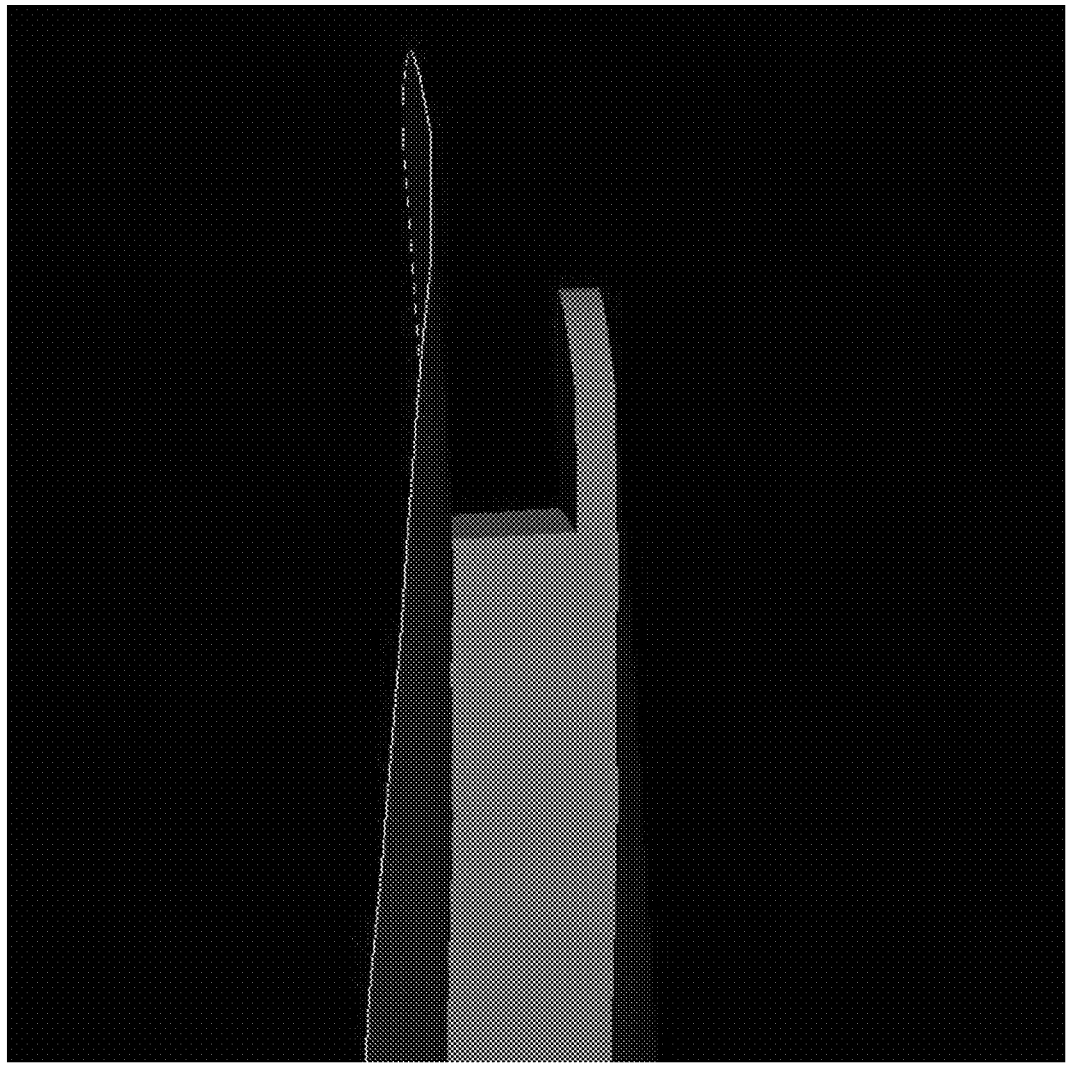
FIG. 11E is a side view of the projection of FIG. 11D showing a divot formed therein to accommodate intersplint wires. The divot is formed by removing sections of the superior and inferior projections to create the lip or divot for wiring.
Figure 11F:
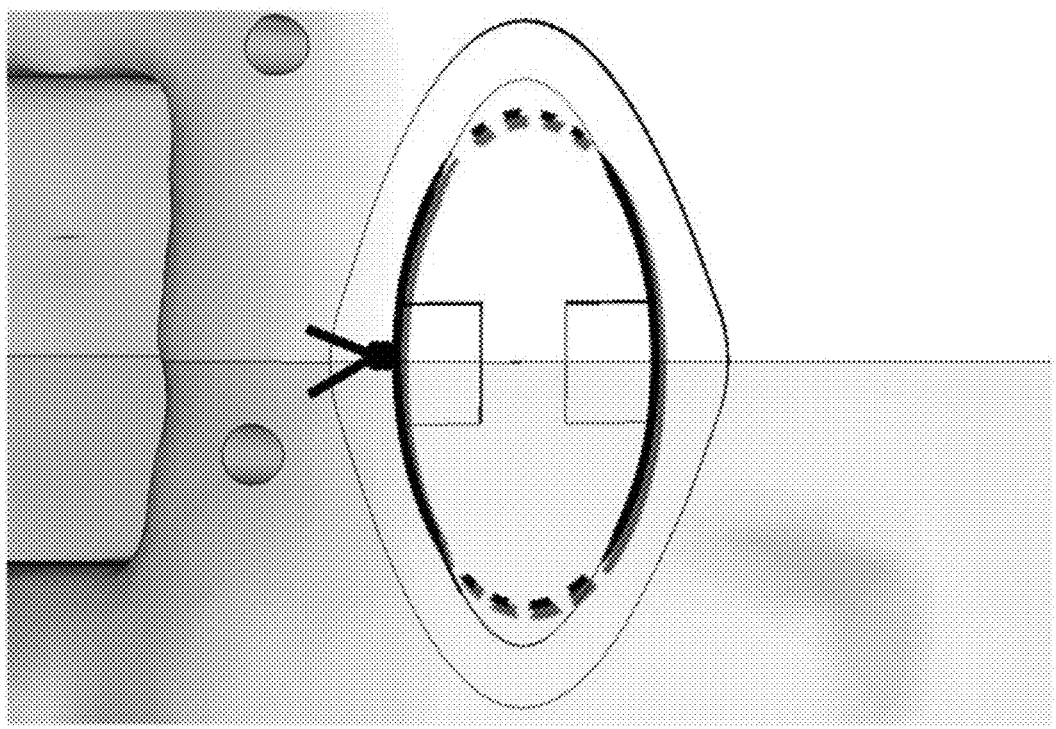
FIG. 11F depicts the projection and divots of FIGS. 11D-11E lassoed with an intersplint wire loop to secure the maxillary splint to the mandibular splint.

As an example of these projections, seen in FIGS. 11B-11F, two recessed ovular protrusions are created on the anterior surface of the splint to allow for anchoring of the upper and lower splints together (FIG. 11F). FIG. 11B shows an oval-shaped drawing of the projection on the sketch plane of FIG. 11A, resulting in the projection being disposed on the anterior surface of the upper and lower splints, as seen in FIG. 11C. It can be appreciated that the sketch plane and drawing can have any suitable shape or size. The oval-shaped sketch creates an extruded surface, as can be seen in FIGS. 11C-11E.

FIG. 11E depicts creation of a divot or recess within the projection to accommodate wiring. The divot or recess is formed by removing sections of the upper and lower projections to create the lip for confining or holding the intersplint wiring. As such, when wiring is lassoed or wrapped around the projection as in FIG. 11F, the upper and lower splints can be held together firmly. The channels of FIG. 11E also permit easy access to cut the intersplint wires, if needed, in order to separate the upper and lower splints from each other.

Figure 12A:
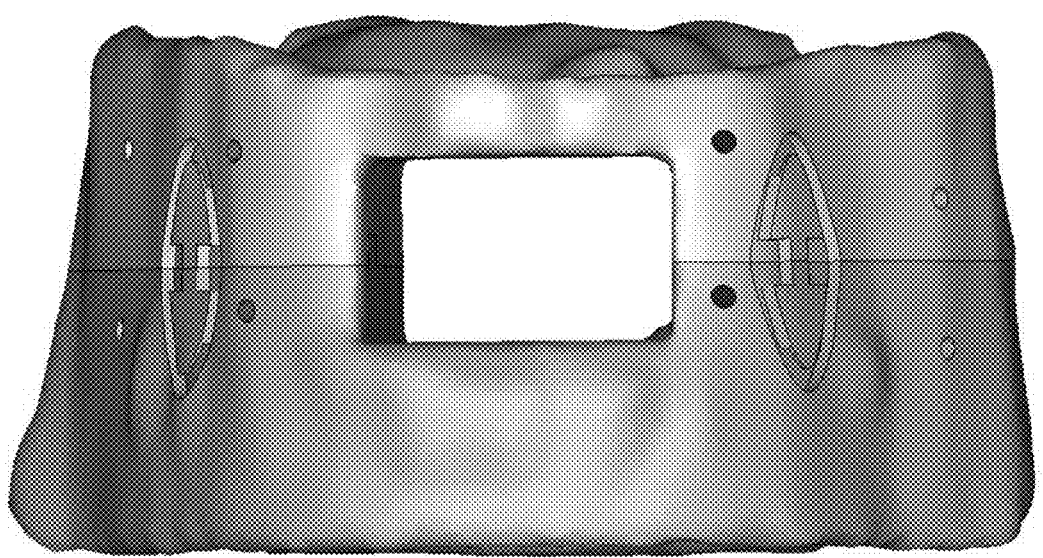
FIG. 12A is an elevated front view of an assembled oral splint according to an embodiment of the current invention.
Figure 12B:
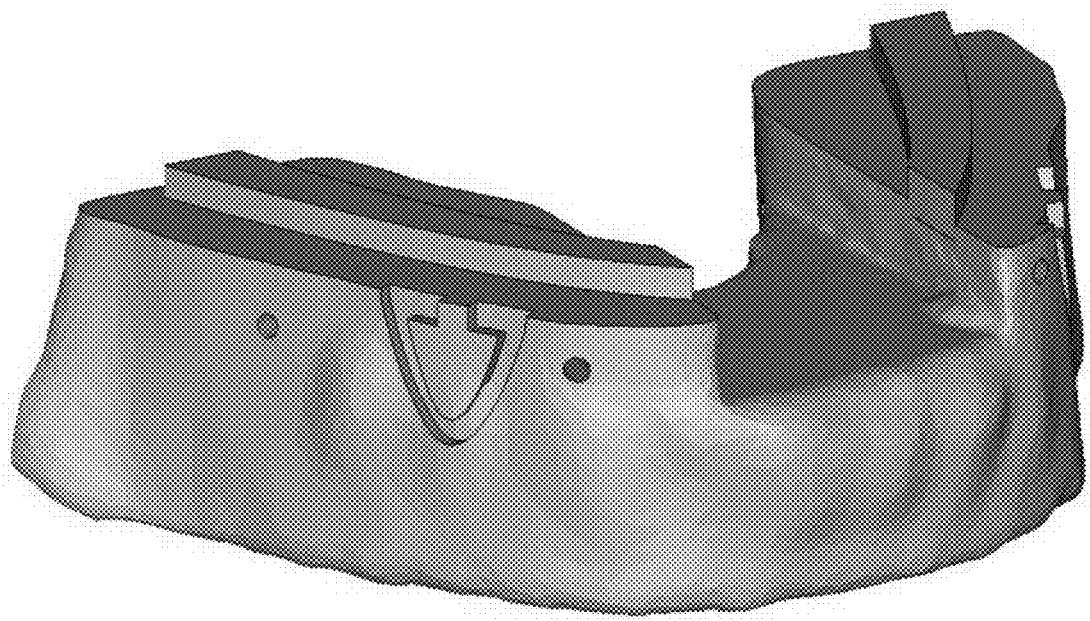
FIG. 12B is a perspective superior view of a mandibular splint of the oral splint of FIG. 12A. It should be noted that the tongue structure is positioned on the mandibular splint in this figure, rather than on the maxillary splint as in FIG. 10C.
Figure 12C:
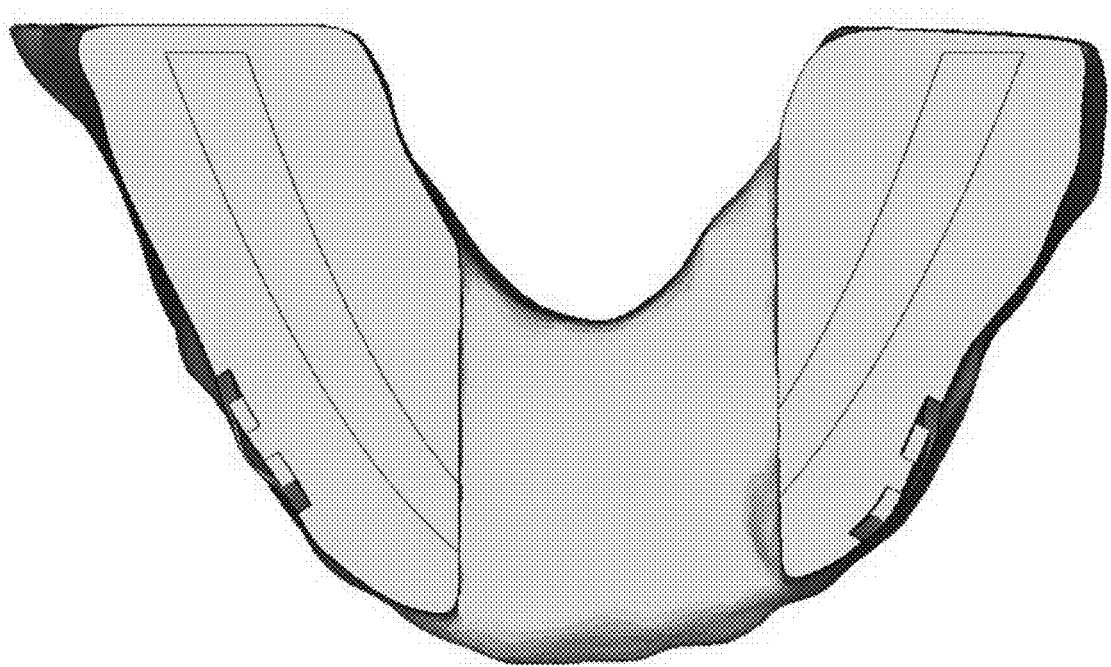
FIG. 12C is a top superior view of the mandibular splint of FIG. 12B.
Figure 12D:
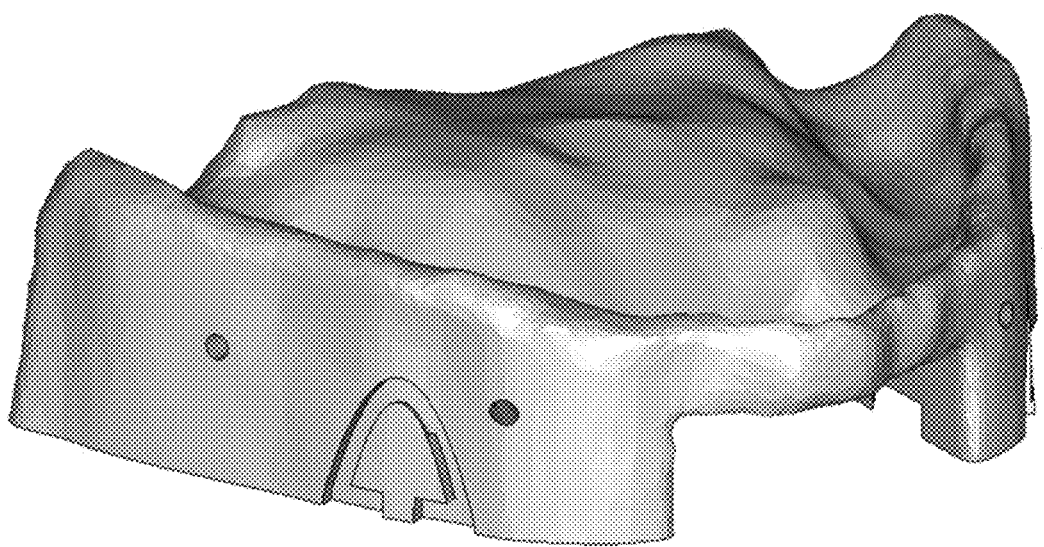
FIG. 12D is a perspective superior view of a maxillary splint of the oral splint of FIG. 12A. It should be noted that the groove structure is positioned on the maxillary splint in this figure (seen by the absence of the tongue structure), rather than on the mandibular splint as in FIG. 10D.
Figure 12E:
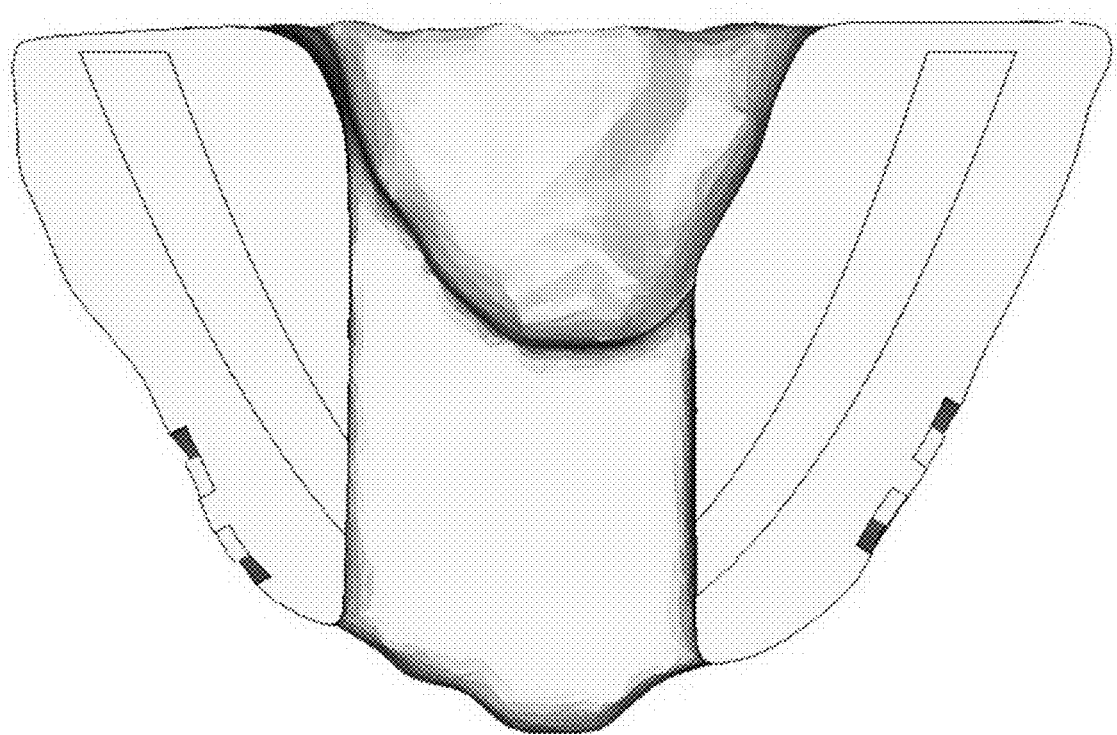
FIG. 12E is a bottom inferior view of the maxillary splint of FIG. 12D.

FIGS. 12A-12E are various views of the resulting virtual image of the splint. FIG. 12A depicts the maxillary and mandibular splint in a closed position. FIGS. 12B-12C depict the mandibular splint with tongue portion disposed thereon, and FIGS. 12D-12E depict the maxillary splint with corresponding groove portion disposed therein.

FIGS. 13A-13E are various views of the splint image in application on a human jaw, both in an exterior view and in a semi-transparent view so that the splint can be seen in comparison to the jaw.

Figure 14:
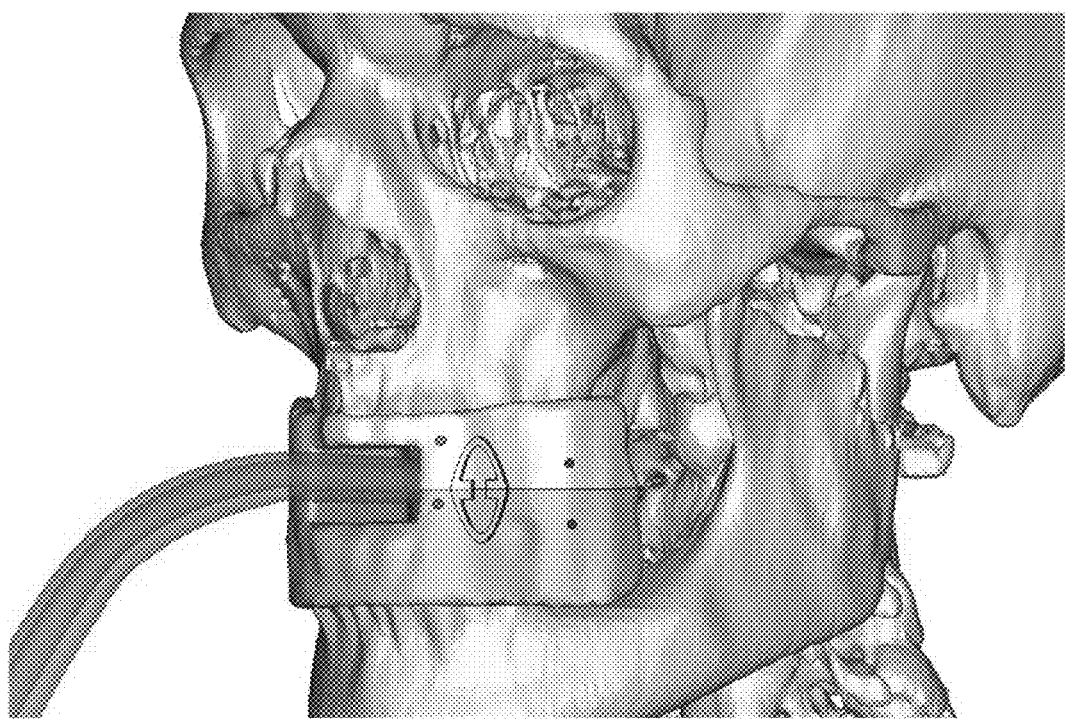
FIG. 14 is a perspective view of an application of an oral splint-resulting from an exemplary methodology according to an embodiment of the current invention-on a human jaw with suctioning instrumentation inserted through the evacuation aperture.

FIG. 14 depicts application of the oral splint, resulting from the methodology described herein, on a human jaw with suctioning instrumentation inserted through the evacuation aperture.

Figure 15A:
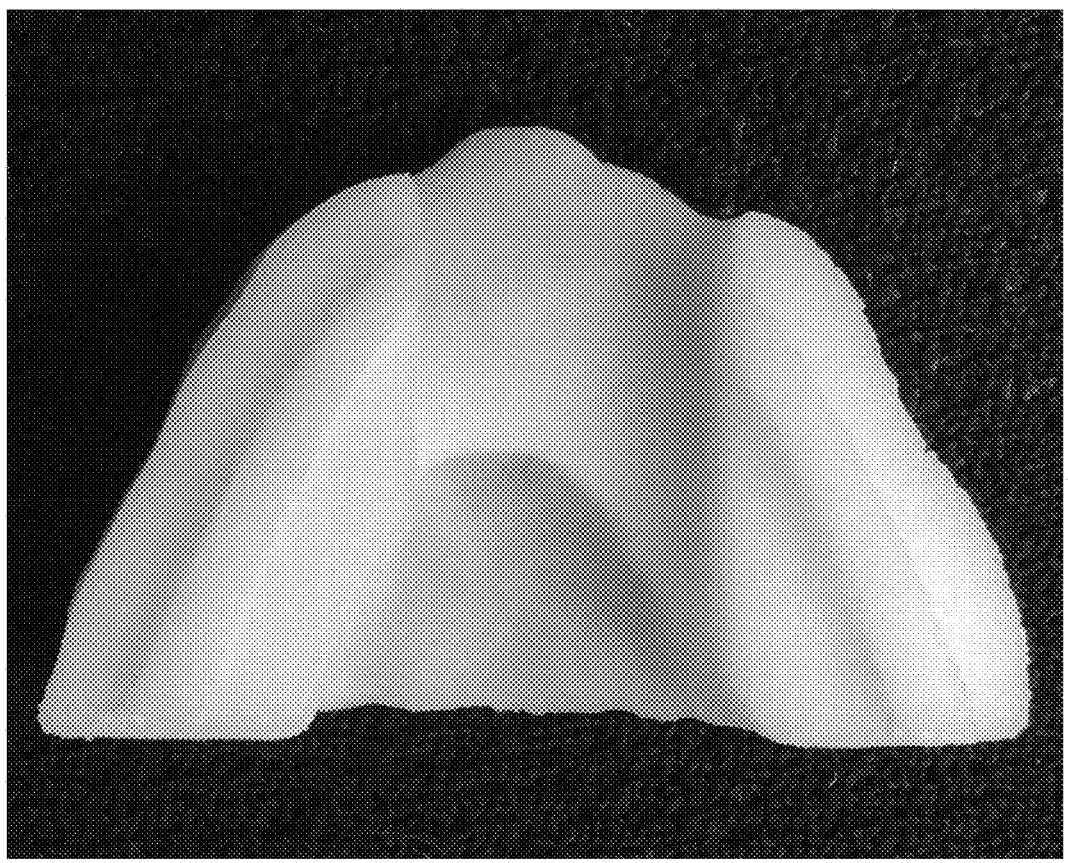
FIG. 15A is a superior view of an exemplary mandibular splint resulting from an embodiment of the novel technique used to fabricate the oral splint.
Figure 15B:
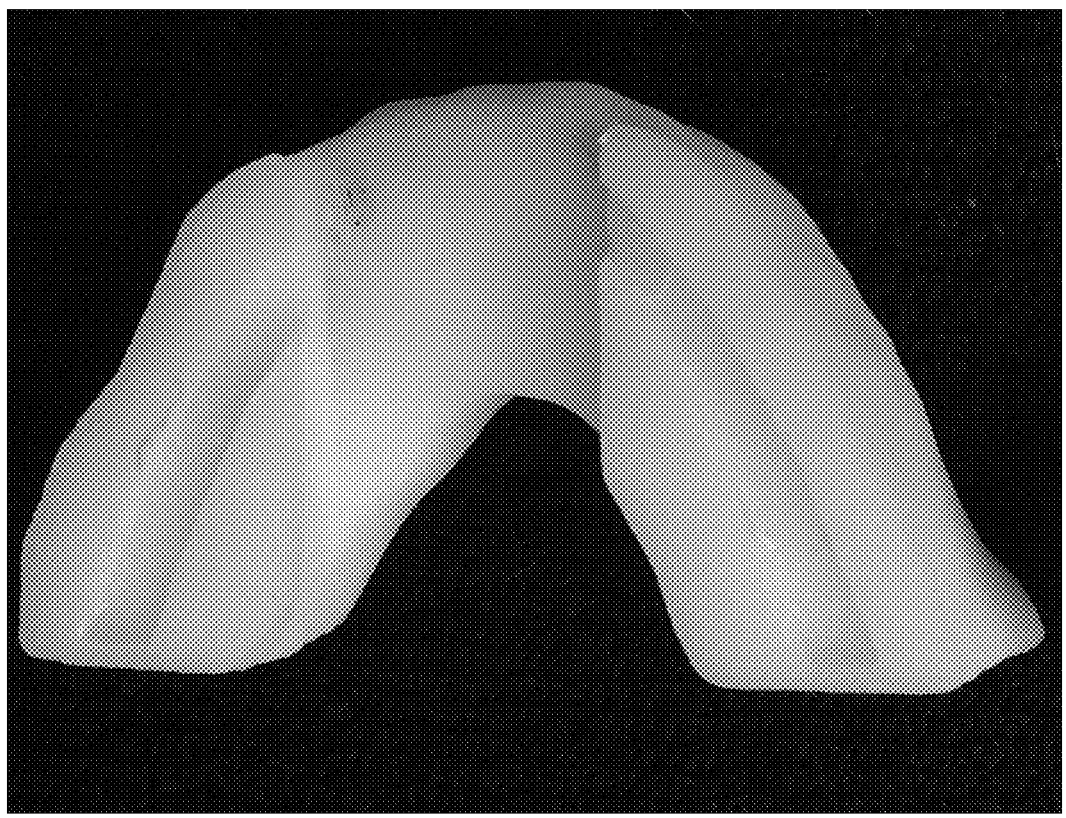
FIG. 15B is an inferior view of an exemplary maxillary splint resulting from an embodiment of the novel technique used to fabricate the oral splint.

Once the resulting splint model (including the maxillary and mandibular splints, tongue and groove fittings/mechanisms, any apertures and/or projections, etc.) is created in virtual space (i.e., on the image processing software), the image can be double-checked and smoothed to prevent any sharp edges from hurting the subject or patient. The model can then be exported and sent to a 3D printer for printing into a physical apparatus, seen in FIGS. 15A-15B, for use by the subject or patient. Once printed, the splint can be sanded to ensure a smooth surface.

Custom Reduction Splint for Edentulous Patients

Once prepared, the custom reduction splint is taken to the operating room with the patient. It is sterilized in a conventional manner, for example with chlorhexidine or betadine in the standard fashion, and then placed in the operative field. The patient is prepped and draped as known in the art. The necessary surgical exposure of the fractures is obtained, and the pyriform aperture of the patient is exposed using methodologies known in the art. The maxillary and mandibular splints are applied in anatomic position to evaluate fit and finalize decisions regarding operative incisions and exposure.

Figure 13A:
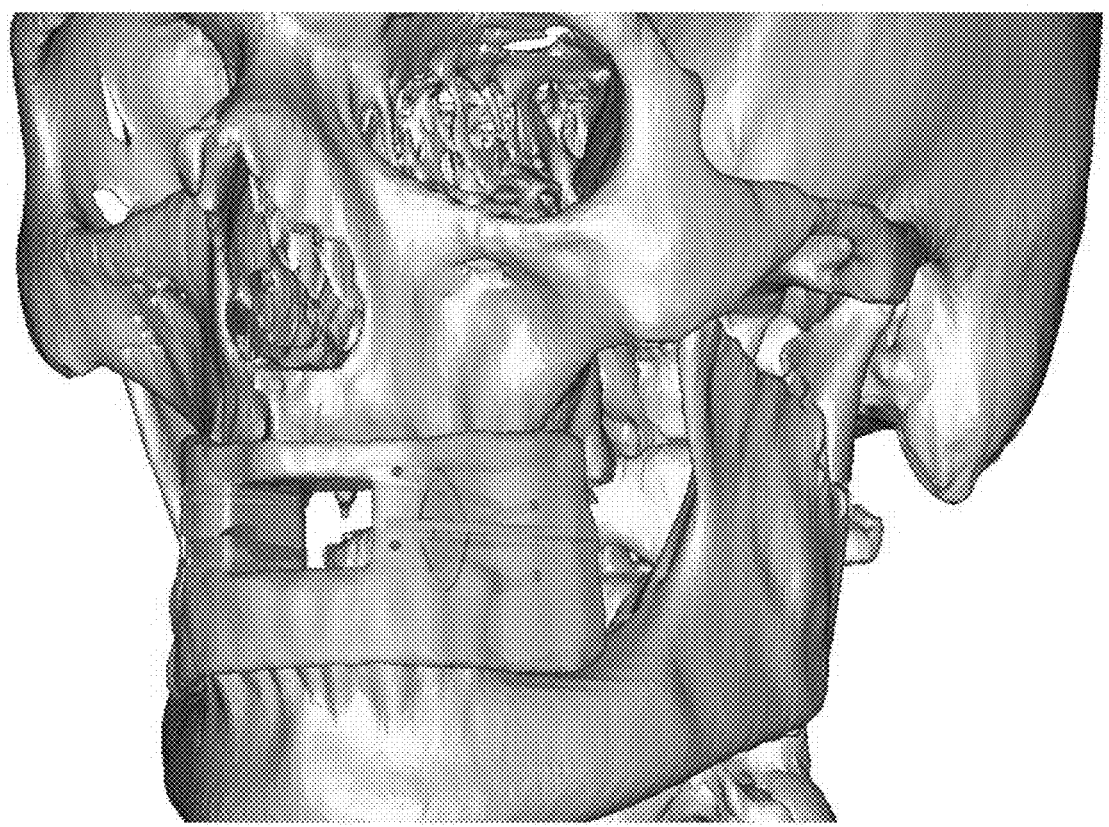
FIG. 13A is a perspective view of an application of an oral splint-resulting from an exemplary methodology according to an embodiment of the current invention-on a human jaw.
Figure 13B:
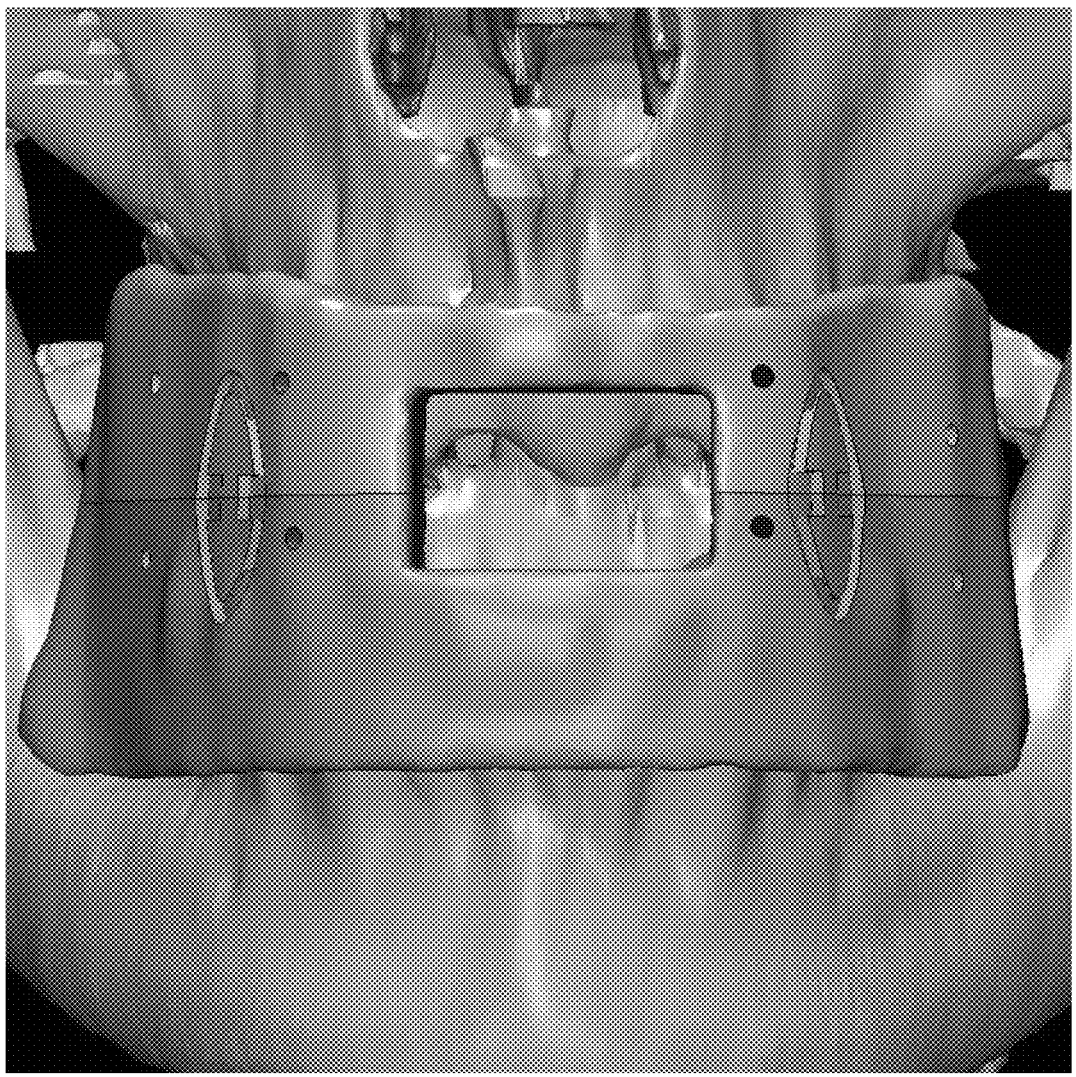
FIG. 13B is a close-up front view of the oral splint of FIG. 13A.
Figure 13C:
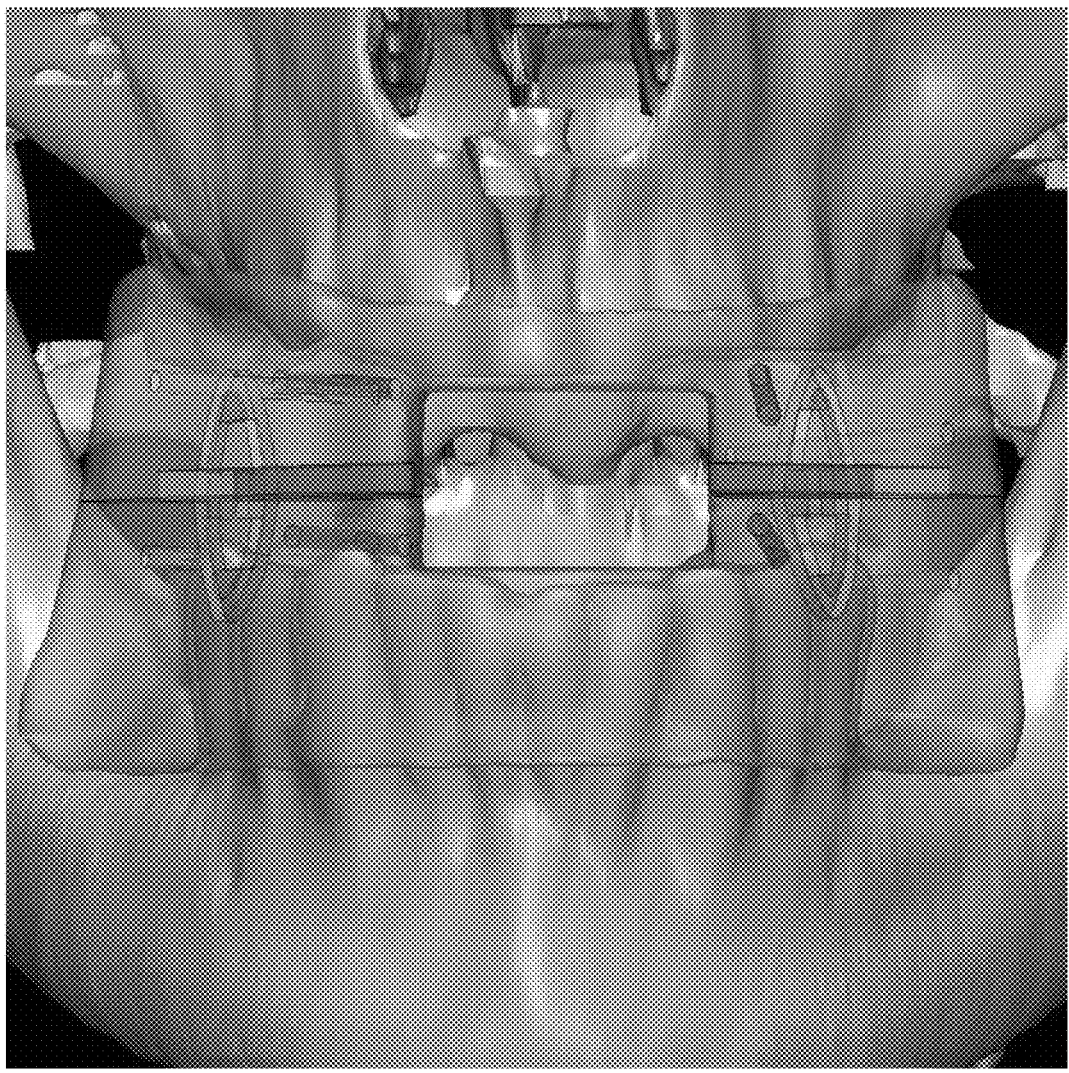
FIG. 13C depicts transparency within the view of FIG. 13B.
Figure 13D:
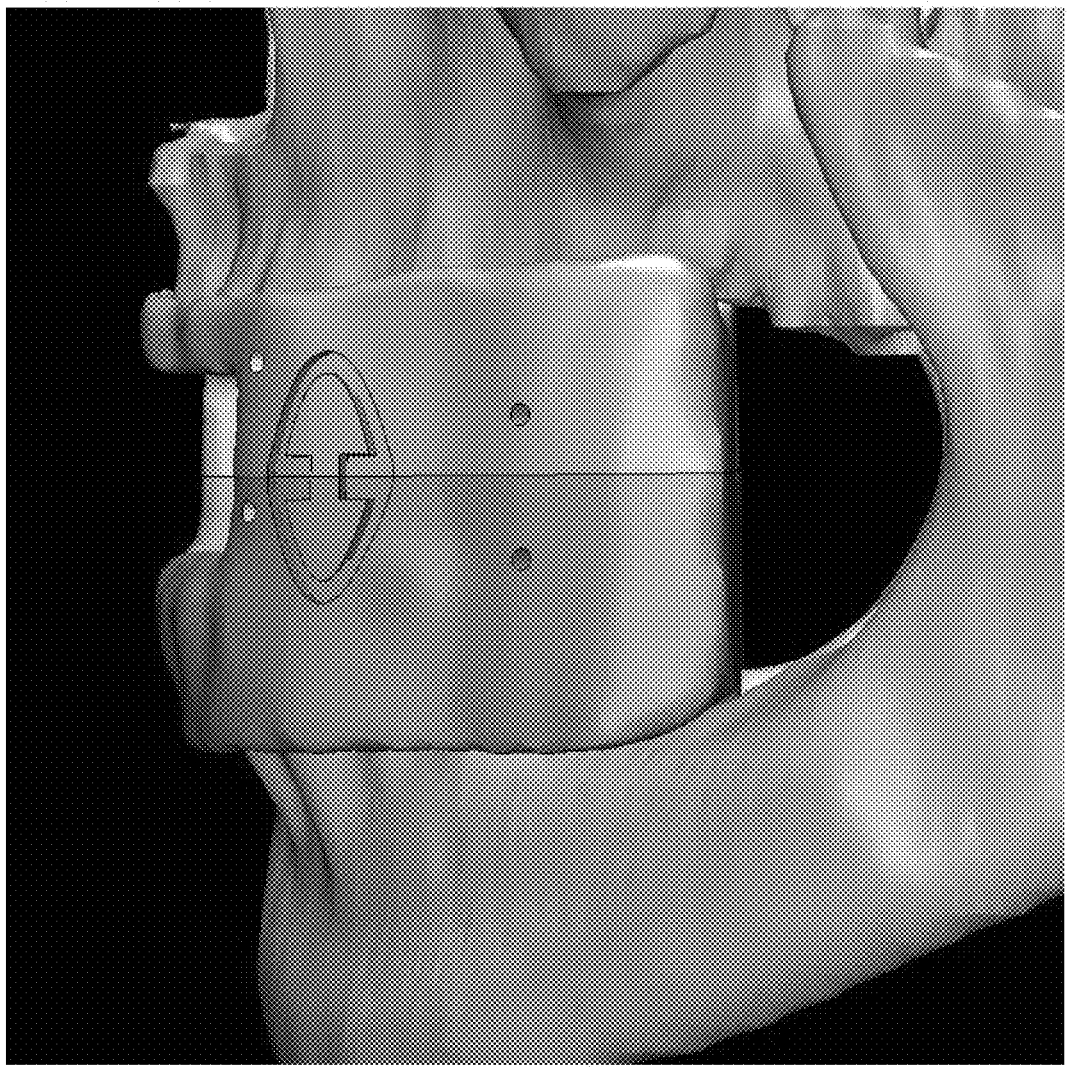
FIG. 13D is a close-up side view of the oral splint of FIG. 13A.
Figure 13E:
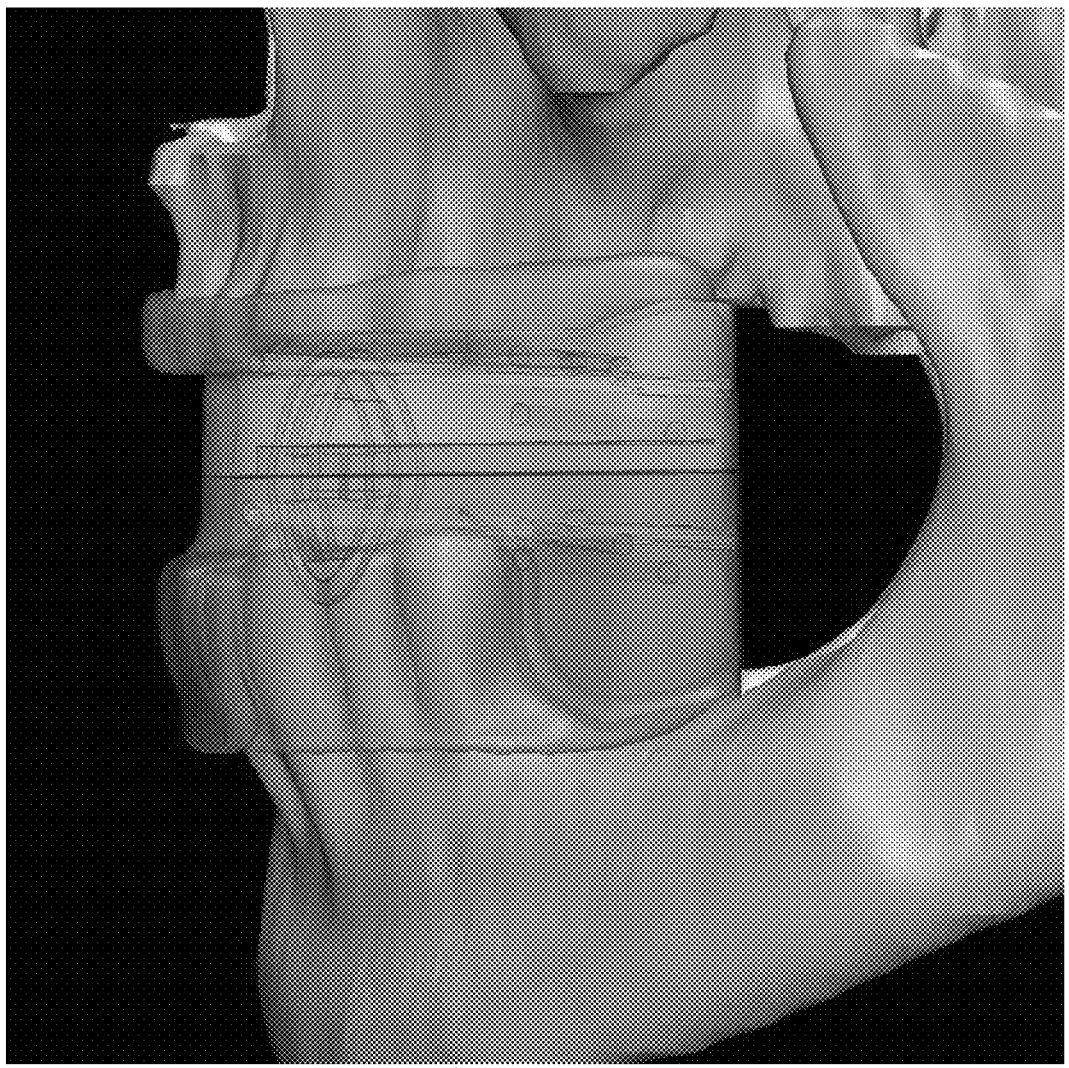
FIG. 13E depicts transparency within the view of FIG. 13D.

As the alveolar ridge and dentition are positioned with the splint into their reduced fracture position, as seen in FIG. 13A, the associated maxillary and/or mandibular fractures can reduce as well, depending on the location and severity of the fractures. To perform this, the maxillary or mandibular splint can be applied/secured first, and the remaining splint can be applied/secured second.

The maxillary splint may be secured to the patient's maxilla by a pyriform drop wire technique, transpalatal-pyriform wire, or similar suitable technique, optionally using the guide wire apertures previously described and seen in FIGS. 8A-8B. A 24-gauge wire can be utilized for either technique, though it can be appreciated that any suitable mechanism can be used. The splint may be removed for initial wire placement to assist with visualization, and subsequently reapplied before tying the wires.

For placing a pyriform drop wire, a 1-mm drill hole can be made approximately 4-5 mm laterally to the inferolateral aspect of the pyriform aperture. The wire is then fed through the drill hole and out the pyriform aperture. The medial wire end is then placed through the anterior opening of the splint and then through the anterior ipsilateral splint hole (passed posterior to anterior), exiting anteriorly from the splint hole. This technique is then repeated on the contralateral side. The medial wire end, now through the splint hole, and the remaining free lateral pyriform wire end are then tied in a conventional manner. The contralateral wires are then similarly tied as well.

Instead of a pyriform drop wire, a transpalatal-pyriform wire (combination of transpalatal wiring and pyriform drop wiring) may be placed to secure the maxillary splint. For the transpalatal-pyriform wire, a standard awl can be used. The awl is placed with steady, firm pressure to the left or right anterior palate, aiming at the base of the ipsilateral pyriform aperture. Once the awl passes through the anterior palate and into the pyriform aperture, the wire is inserted into the awl's terminal hole, and the awl is retracted into the mouth, pulling the wire with it. The same procedure is repeated on the contralateral side. The maxillary splint can then be positioned anatomically, followed by tying the free wire ends over the splint, tightly securing it to the maxilla.

It can be appreciated by one of ordinary skill in the art that the current invention contemplates other suitable methodologies of securing the maxillary splint to the maxilla as well, as would be known in the art.

To secure the mandibular splint to the patient's mandible, optionally using the guide wire apertures previously described and seen in FIGS. 8A-8B, an awl can used in a conventional manner to position four circummandibular wires, one anterior and one posterior on each side. The lingual wire end of each circummandibular wire is then fed from posterior to anterior through the corresponding mandibular splint holes. The splint is positioned anatomically, and the lingual and buccal wire ends of each circummandibular wire are then tied in a conventional manner, thus securing the splint tightly to the mandible.

It can be appreciated by one of ordinary skill in the art that the current invention contemplates other suitable methodologies of securing the mandibular splint to the mandible as well, as would be known in the art.

With both the maxillary splint and the mandibular splint secured to the maxilla and mandible, respectively, the maxillary and mandibular splints can be secured to one another, for example by intersplint wires tied around the projections on the anterior surface of the splint, as previously described and seen in FIGS. 11A-11F. Standard 24-gauge or similar wire loops can be utilized. The recessed, oval-shaped projections spanning the maxillary and mandibular splints are lassoed with the wire loop, as seen in FIG. 11F. The wire loop is then tightened in the standard fashion around the recessed projection, one on each side of the central evacuation aperture.

The maxillary and mandibular splints may be further stabilized together in any particular manner, for example the tongue-and-groove mechanism/fitting as previously described and seen in FIGS. 10A-10D.

Additional wires may be placed at the discretion of the surgeon or operating team. The splints may be drilled with a standard drill bit or k-wire, using a steady hand and irrigation to minimize thermal damage to the surrounding splint material.

No mandibular incisions are required for splint placement if the patient has at least a majority of his/her teeth. This contrasts conventional technology where mandibular incisions are necessary in all cases with unstable mandibular fractures, regardless of how many teeth the patient possesses. However, incisions may be required with the current methodology if additional fracture fixation is indicated, specifically near the posterior portion of the mandible.

For maxillary splint placement, only two (2) limited maxillary buccal sulcus incisions are utilized to provide visualization of the pyriform aperture. These incisions may be closed with conventional techniques after the intersplint wires are positioned to secure the maxillary and mandibular splints to one another.

In an emergency situation, the intersplint wires can be cut easily to allow access to the patient's mouth and/or airway, though fracture reduction or posterior mandibular height may be lost. The patient can carry wire cutters in an accessible location, should there be a need for someone else to cut the patient's wires to release the splint. The intersplint wires can be reapplied without sedation, as long as the patient can tolerate the tongue-and-groove realignment of the maxillary and mandibular splints and as long as the maxillary and mandibular splints remain secure in an anatomic position.

Optionally, depending on the treatment plan decided on by the operating surgeon, the intersplint wires may be intentionally cut and elastics positioned around the recessed projections to provide a limited range of motion.

For removal of the reduction splint, the pyriform and circummandibular wires are cut at the level of the mucosa, and the wires are removed. Care should be taken to limit the tracking of oral contents through the wire tunnel as the wires are removed. The maxillary and mandibular splints are then easily removed. The empty wire tunnel does not need to be sutured, but it can be left to heal secondarily.

Standard operative techniques to reduce infection risk still apply, such as, but not limited to, irrigation, pre-operative/post-operative antibiotics, and routine oral hygiene procedures.

Experiment/Study

The following study examines the role of computerized 3D modeling and rapid prototyping of mandibular fractures in edentulous and partially edentulous patients with the aim of generating a patient-specific splint to aid in fracture reduction and union.

Methods

Participants for this study were selected from edentulous and partially edentulous patients that presented with displaced mandibular fractures. Once selected, diagnostic medical images were used for analysis and pre-operative planning. For each case, a computer tomography (CT) scan of the patient's maxilla and mandible was imported into the software package MIMICS by MATERIALISE. The fractured bone structures of the maxilla and mandible were segmented and tessellated into 3D models. The bone fragments were aligned virtually into appropriate reduction, and the mandible was then placed into anatomic position. With the maxilla and mandible structurally intact and in anatomic relationship, the splint was designed by creating a "U-shape" on the upper and lower palates and interpolating the distance between them as a solid. Once this model was made, the stereolithographic files (STL) were imported into 3-MATIC. From there, the bony 3D anatomy was wrapped with a 1-mm detail parameter and protect thin walls parameter to disfeature and slightly expand the native bone and dentition. Using a Boolean subtraction, the bone was subtracted from the splint. The circumferential gingival coverage of the splint was checked to ensure the abutting lingual and buccal sulci were not impinged. Any areas of impingement were adjusted accordingly.

For patient safety, a rectangular hole of about 12-mm height and about 20-mm width was centered anteriorly to accommodate oral suction instrumentation and permit escape of the patient's oral secretions and/or emesis. The splint was cut horizontally into top and bottom halves/portions; the top corresponds to the maxilla, and the bottom corresponds to the mandible. Eight (8) 1.5-mm diameter apertures were then placed in the top and bottom portions of the splint (four in each half) to allow for fixation to the maxilla and mandible, respectively, with standard 24-gauge wire. Two recessed oval-shaped projections/tabs were also created on the anterior surface of the splint to allow for anchoring of the two halves together with intersplint wires. Divots or channels within these oval-shaped tabs allowed for rapid cutting of the intersplint wires, in the event emergency access to the patient's airway was needed.

Once the model was created in virtual space, it was double-checked for any harmful edges and smoothed accordingly. An STL file is then sent to a desktop rapid prototype machine, CUBEX DUO, for printing. Once printed, the model was manually sanded and inspected to ensure a smooth surface.

Results

The patient-specific splints were sterilized in a chemical bath and surgically applied to each patient. The presence of the splint with predrilled holes provided greater efficiency in the operating room, and the surgeons noted that fewer surgical instruments were utilized than with conventional techniques. There was excellent fit of the splints to the patient's anatomy, and the fractures remained stabilized in appropriate alignment during the postoperative splinting period. After the appropriate time for bony consolidation of fractures, the splint was removed. Several patients were successfully treated in this manner, exhibiting superior clinical outcomes.

Thus, it can be concluded that a patient-specific splint can be generated from computerized 3D modeling of and mandibular fractures in edentulous and partially edentulous patients, and it can effectively treat these fractures as well. This provides maxillofacial surgeons with an efficient, cost-effective, patient-specific option for the correction of jaw fractures.

GLOSSARY OF CLAIM TERMS

Anterior-posterior plane: This term is used herein to refer to an imaginary flat surface disposed in a direction between the front of the subject or patient and the back of the subject or patient, such that the upper face of the plane faces the cranial direction and the lower face of the plane faces the caudal direction.

Cranial-caudal direction: This term is used herein to refer to a disposition of something along a route between the head end of the body and the tail end of the body, which is typically a substantially vertical direction in a human being. On the other hand, in a four-legged animal, for example, the cranial-caudal direction can refer to a disposition between the head end of that animal and the ground on which the animal stands (rather than the actual tail end of the animal).

Distance: This term is used herein to refer to the amount of space between the outline of the upper palate and the outline of the lower palate.

Edentulous or partially edentulous: This term is used herein to refer to a subject or patient of any age being toothless to at least some degree due to one or more teeth being loose or absent. Complete edentulism refers to the absence of all teeth, whereas partial edentulism refers to the absence one or more teeth.

Evacuation aperture: This term is used herein to refer to an opening in the front of the splint used for evacuation of oral or gastric contents from the patient as needed, thus preventing aspiration.

Imaging: This term is used herein to refer to the creation of visual representations of the interior of a body of a subject or patient. These representations can be used for medical therapy, such as oral fracture reduction as enabled by the present invention. Examples of imaging include, but are not limited to, X-ray radiography, magnetic resonance imaging, computed tomography, medical ultrasonography or ultrasound, endoscopy, elastography, tactile imaging, thermography, medical photography and positron emission tomography.

Initial splint configuration: This term is used herein to refer to a preliminary representation of the oral splint being fabricated prior to finalization of the digital image of the splint.

Intersplint wires: This term is used herein to refer to wiring that secures together a mandibular splint and a corresponding maxillary splint.

Jaw: This term is used herein to refer to the mandibular and/or maxillary bones and their associated soft tissue and dentition.

Normal position: This term is used herein to refer to the anatomic arrangement of bone and dentition in a subject or patient as present prior to oral fractures.

Oral fracture: This term is used herein to refer to breaks through the mandibular or maxillary bone or dentition of a subject or patient.

Oral splint: This term is used herein to refer to a device used in the oral cavity of a subject or patient to affix the maxilla and mandible in place during oral fracture reduction.

Outline: This term is used herein to refer to sketching or creating a line or contour along the boundary of a structure, such as the upper and lower palates of a subject or patient.

Outwardly: This term is used herein to refer to a direction toward the exterior of the splint or toward the exterior of the oral cavity of the subject or patient if the splint was hypothetically in place in the oral cavity. The virtual dentition size is increased so that the fit may be loosened and the splint may be more easily applied.

Palate: This term is used herein to refer to the floor (lower palate) and/or roof (upper palate) of the subject or patient's mouth, including the bone and the associated soft tissue.

Realign: This term is used herein to refer to the process of rearranging structures, such as bone and dentition, of a subject or patient into a "normal" or healthy position where the structures would be in that subject or patient without fracture.

Reduced fracture position: This term is used herein to refer to an arrangement of a splint in/on a subject or patient, such that any potential fracture of the underlying bone/dentition would be aligned properly.

Snugly fit or contain: This term is used herein to refer to lining the splint along the exterior surface of the subject or patient's dentition/bone.

Split: This term is used herein to refer to dividing a structure into two or more parts/portions along a relatively straight line through the structure.

Tongue and groove fitting: This term is used herein to refer to a joint for fitting structures together, where one of the structures has a protrusion and the other structure has a channel in which the protrusion fits.

Wire aperture: This term is used herein to refer to a small opening allowing for the traversal of wiring that secures the mandibular splint to the mandible, the maxillary splint to the maxilla, and/or the mandibular splint to the maxillary splint.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of fabricating an oral splint for reduction of an oral fracture in an edentulous or partially edentulous subject or patient, comprising:
   scanning or imaging a jaw of said subject or patient;
   importing results of said scanning or imaging into one or more software applications that segments a maxilla and a mandible of said jaw;
   realigning said fracture within said maxilla or said mandible on said one or more software applications into a normal position;
   outlining an upper palate of said jaw on said one or more software applications;
   outlining a lower palate of said jaw on said one or more software applications;
   interpolating a distance between said outline of said upper palate and said outline of said lower palate on said one or more software applications;
   indicating said distance as an initial splint configuration on said one or more software applications;
   removing bone and dentition of said maxilla and said mandible from said image of said jaw on said one or more software applications; and
   splitting said initial splint configuration into a maxillary splint and a mandibular splint on said one or more software applications, thus forming a virtual image of said oral splint, wherein said oral splint is fabricated physically based on said virtual image of said oral splint.

2. A method as in claim 1, further comprising:
   tessellating said maxilla and said mandible into a three-dimensional model after importing said results of said scanning or imaging into said one or more software applications.

3. A method as in claim 1, further comprising:
   expanding said initial splint configuration outwardly to snugly fit or contain said maxilla and said mandible in said normal position.

4. A method as in claim 1, further comprising:
   forming an evacuation aperture in an anterior portion of said initial splint configuration, wherein an upper portion of said evacuation aperture is disposed in said anterior portion of said maxillary splint and a lower portion of said evacuation aperture is disposed in said anterior portion of said mandibular splint.

5. A method as in claim 1, further comprising:
   the step of splitting said initial splint configuration performed by positioning an anterior-posterior plane within a midsection of said initial splint configuration, wherein the position of said plane in a cranial-caudal direction is based on a presence or absence of teeth within said jaw of said subject or patient, and
   separating said maxillary splint and said mandibular splint along said plane.

6. A method as in claim 1, further comprising:
   disposing an extrusion on one of a superior surface of said mandibular splint or an inferior surface of said maxillary splint on said one or more software applications;
   disposing a channel in the other of said superior surface of said mandibular splint or said inferior surface of said maxillary splint that did not receive said extrusion on said one or more software applications, wherein a position of said channel corresponds to a position of said extrusion,
   said extrusion and said channel forming a tongue and groove fitting between said maxillary splint and said mandibular splint.

7. A method as in claim 6, further comprising:
   said extrusion being U-shaped along a jaw line of said subject or patient, and
   said channel being U-shaped along said jaw line of said subject or patient.

8. A method as in claim 1, further comprising:
   disposing a first maxillary projection and a second maxillary projection on said maxillary splint; and
   disposing a first mandibular projection and a second mandibular projection on said mandibular splint,
   wherein said first maxillary projection and said first mandibular projection are aligned with each other, and
   wherein said second maxillary projection and said second mandibular projection are aligned with each other.

9. A method as in claim 1, further comprising:
   prior to outlining said upper and lower palates, positioning a spacer on said maxilla or said mandible of said subject or patient on said one or more software applications in order to provide proper spacing within said jaw of said subject or patient.

10. A surgical technique for reduction of an oral fracture in an edentulous or partially edentulous subject or patient, comprising:
    scanning or imaging a jaw of said subject or patient;
    importing results of said scanning or imaging into one or more software applications that segments a maxilla and a mandible of said jaw;
    realigning said fracture within said maxilla or said mandible on said one or more software applications into a normal position;
    outlining an upper palate of said jaw on said one or more software applications;
    outlining a lower palate of said jaw on said one or more software applications;
    interpolating a distance between said outline of said upper palate and said outline of said lower palate on said one or more software applications;
    indicating said distance as an initial splint configuration on said one or more software applications;
    removing bone and dentition of said maxilla and said mandible from said image of said jaw on said one or more software applications;
    splitting said initial splint configuration into a maxillary splint and a mandibular splint on said one or more software applications, thus forming a virtual image of said oral splint;
    fabricating said oral splint based on said virtual image of said oral splint;
    positioning and securing said maxillary splint of said fabricated oral splint on said maxilla of said subject or patient in a normal or reduced fracture position of said maxilla; and
    positioning and securing said mandibular splint of said fabricated oral splint on said mandible of said subject or patient in a normal or reduced fracture position of said mandible.

11. A surgical technique as in claim 10, further comprising:
    tessellating said maxilla and said mandible into a three-dimensional model after importing said results of said scanning or imaging into said one or more software applications.

12. A surgical technique as in claim 10, further comprising:
    expanding said initial splint configuration outwardly to snugly fit or contain said maxilla and said mandible in said normal position.

13. A surgical technique as in claim 10, further comprising:
forming an evacuation aperture in an anterior portion of said initial splint configuration, wherein an upper portion of said evacuation aperture is disposed in said anterior portion of said maxillary splint and a lower portion of said evacuation aperture is disposed in said anterior portion of said mandibular splint.

14. A surgical technique as in claim 10, further comprising:
the step of splitting said initial splint configuration performed by positioning an anterior-posterior plane within a midsection of said initial splint configuration, wherein the position of said plane in a cranial-caudal direction is based on a presence or absence of teeth within said jaw of said subject or patient, and
separating said maxillary splint and said mandibular splint along said plane.

15. A surgical technique as in claim 10, further comprising:
disposing an extrusion on one of a superior surface of said mandibular splint or an inferior surface of said maxillary splint on said one or more software applications;
disposing a channel in the other of said superior surface of said mandibular splint or said inferior surface of said maxillary splint that did not receive said extrusion on said one or more software applications, wherein a position of said channel corresponds to a position of said extrusion,
said extrusion and said channel forming a tongue and groove fitting between said maxillary splint and said mandibular splint.

16. A surgical technique as in claim 15, further comprising:
said extrusion being U-shaped along a jaw line of said subject or patient, and
said channel being U-shaped along said jaw line of said subject or patient.

17. A surgical technique as in claim 10, further comprising:
disposing a first maxillary projection and a second maxillary projection on said maxillary splint; and
disposing a first mandibular projection and a second mandibular projection on said mandibular splint,
wherein said first maxillary projection and said first mandibular projection are aligned with each other, and
wherein said second maxillary projection and said second mandibular projection are aligned with each other.

18. A surgical technique as in claim 17, further comprising:
securing said maxillary splint and said mandibular splint together via intersplint wires wrapped around said first maxillary projection and said first mandibular projection and also around said second maxillary projection and said second mandibular projection.

19. A surgical technique as in claim 10, further comprising:
prior to outlining said upper and lower palates, positioning a spacer on said maxilla or said mandible of said subject or patient on said one or more software applications in order to provide proper spacing within said jaw of said subject or patient.

20. A surgical technique for reduction of an oral fracture in an edentulous or partially edentulous subject or patient, comprising:
scanning or imaging a jaw of said subject or patient;
importing results of said scanning or imaging into one or more software applications that segments a maxilla and a mandible of said jaw;
tessellating said maxilla and said mandible into a three-dimensional model;
realigning said fracture within said maxilla or said mandible on said one or more software applications into a normal position;
positioning a spacer on said maxilla or said mandible of said subject or patient on said one or more software applications in order to provide proper spacing within said jaw of said subject or patient;
outlining an upper palate of said jaw on said one or more software applications;
outlining said maxilla of said jaw on said one or more software applications;
outlining a lower palate of said jaw on said one or more software applications;
outlining said mandible of said jaw on said one or more software applications;
interpolating a distance between said outline of said upper palate and said outline of said lower palate on said one or more software applications;
indicating said distance as an initial splint configuration on said one or more software applications;
expanding said initial splint configuration outwardly to snugly fit or contain said maxilla and said mandible in said normal position;
trimming or filing an upper edge or a lower edge of said initial splint configuration to better fit said jaw of said subject or patient;
removing bone and dentition of said maxilla and said mandible from said image of said jaw on said one or more software applications;
forming an evacuation aperture in an anterior portion of said initial splint configuration;
splitting said initial splint configuration into a maxillary splint and a mandibular splint on said one or more software applications, thus forming a virtual image of said oral splint, wherein an upper portion of said evacuation aperture is disposed in said anterior portion of said maxillary splint and a lower portion of said evacuation aperture is disposed in said anterior portion of said mandibular splint,
wherein the step of splitting said initial splint configuration is performed by
positioning an anterior-posterior plane within a midsection of said initial splint configuration, wherein the position of said plane in a cranial-caudal direction is based on a presence or absence of teeth within said jaw of said subject or patient, and
separating said maxillary splint and said mandibular splint along said plane;
forming a plurality of wire apertures in said maxillary splint and said mandibular splint to accommodate wiring to secure said maxillary splint to said maxilla and to accommodate wiring to secure said mandibular splint to said mandible;
disposing an extrusion on one of a superior surface of said mandibular splint or an inferior surface of said maxillary splint on said one or more software applications;
disposing a channel in the other of said superior surface of said mandibular splint or said inferior surface of said maxillary splint that did not receive said extrusion on said one or more software applications, wherein a position of said channel corresponds to a position of said extrusion,
said extrusion being U-shaped along a jaw line of said subject or patient and said channel being U-shaped along said jaw line of said subject or patient, wherein said extrusion and said channel form a tongue and groove fitting between said maxillary splint and said mandibular splint;
disposing a first maxillary projection and a second maxillary projection on said maxillary splint;

disposing a first mandibular projection and a second mandibular projection on said mandibular splint, wherein said first maxillary projection and said first mandibular projection are aligned with each other, and wherein said second maxillary projection and said second mandibular projection are aligned with each other, said first and second maxillary projections and said first and second mandibular projections including divots;

fabricating said oral splint based on said virtual image of said oral splint by transmitting said virtual image to a three-dimensional printer for printing of said oral splint;

positioning and securing said maxillary splint of said fabricated oral splint on said maxilla of said subject or patient in a normal or reduced fracture position of said maxilla, wherein the step of securing said maxillary splint on said maxilla of said subject or patient is performed by a mechanism selected from the group consisting of a pyriform drop wire and transpalatal-pyriform wire;

positioning and securing said mandibular splint of said fabricated oral splint on said mandible of said subject or patient in a normal or reduced fracture position of said mandible, wherein the step of securing said mandibular splint on said mandible of said subject or patient is with circummandibular wires performed by utilizing an awl; and securing said maxillary splint and said mandibular splint together via intersplint wires wrapped around said first maxillary projection and said first mandibular projection within said divots and also around said second maxillary projection and said second mandibular projection within said divots.

\* \* \* \* \*